US011630110B2

(12) United States Patent
Tan

(10) Patent No.: US 11,630,110 B2
(45) Date of Patent: Apr. 18, 2023

(54) METHODS TO IDENTIFY PROTEIN INTERACTION

(71) Applicant: AGENCY FOR SCIENCE, TECHNOLOGY AND RESEARCH, Singapore (SG)

(72) Inventor: Soon Heng Tan, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 542 days.

(21) Appl. No.: 16/632,646

(22) PCT Filed: Aug. 20, 2018

(86) PCT No.: PCT/SG2018/050422
§ 371 (c)(1),
(2) Date: Jan. 21, 2020

(87) PCT Pub. No.: WO2019/035773
PCT Pub. Date: Feb. 21, 2019

(65) Prior Publication Data
US 2020/0166520 A1 May 28, 2020

(30) Foreign Application Priority Data
Aug. 18, 2017 (SG) .......................... 10201706788W

(51) Int. Cl.
*G01N 33/68* (2006.01)
(52) U.S. Cl.
CPC ..... *G01N 33/6845* (2013.01); *G01N 33/6848* (2013.01)

(58) Field of Classification Search
None
See application file for complete search history.

(56) References Cited

U.S. PATENT DOCUMENTS

| 2014/0057368 A1 | 2/2014 | Nordlund |
| 2017/0010229 A1* | 1/2017 | Moritz ............... H01J 49/0036 |

FOREIGN PATENT DOCUMENTS

| CN | 103733067 A | 4/2014 |
| CN | 106233144 A | 12/2016 |

(Continued)

OTHER PUBLICATIONS

Molina et al., "Monitoring Drug Target Engagement in Cells and Tissues Using the Cellular Thermal Shift Assay", Science, vol. 341, No. 6141, Jul. 5, 2013, pp. 84-87.

(Continued)

*Primary Examiner* — Xiaoyun R Xu
(74) *Attorney, Agent, or Firm* — Marshall, Gerstein & Borun LLP

(57) ABSTRACT

The present invention discloses methods for identifying a protein interaction between one or more first proteins and one or more further proteins comprising the steps of: exposing one or more samples comprising the proteins to at least one preselected condition for at least one preselected duration; isolating and separating at least one soluble fraction from an insoluble fraction of said one or more samples; and analyzing the at least one soluble fraction or the insoluble fraction to identify said protein interaction between one or more first proteins and one or more further proteins. Use of the method of the invention are also disclosed.

19 Claims, 32 Drawing Sheets

(56) References Cited

FOREIGN PATENT DOCUMENTS

| | | |
|---|---|---|
| WO | WO-2012/143714 A1 | 10/2012 |
| WO | WO-2015/145151 A1 | 10/2015 |
| WO | WO-2017/007849 A1 | 1/2017 |

OTHER PUBLICATIONS

Tan et al., "Thermal Proximity Coaggregation for System-wide Profiling of Protein Complex Dynamics in Cells", Science, vol. 359, No. 6380, Feb. 8, 2018, pp. 1170-1177.
Huttlin et al., "Architecture of the Human Interactome Defines Protein Communities and Disease Networks", Nature, vol. 545, No. 7655, May 25, 2017, pp. 505-509.
Cafarelli et al., "Mapping, Modeling, and Characterization of Protein-protein Interactions on a Proteomic Scale", Curr Opin Struct Biol, vol. 44, May 30, 2017, pp. 201-210.
Snider et al., "Fundamentals of Protein Interaction Network Mapping", Mol Syst Biol, vol. 11, No. 12, Dec. 17, 2015, 20 pages.
Search Report and Written Opinion in International Application No. PCT/SG2018/050422 dated Nov. 9, 2018, 11 pages.
First Office Action for Chinese Application No. 2018800677668, dated Feb. 16, 2023.

\* cited by examiner

A

B

B

A    B

A

B

A

B

C

D

A

B

C

A

B

METHODS TO IDENTIFY PROTEIN INTERACTION

CROSS-REFERENCE TO RELATED APPLICATIONS

This application claims the benefit of priority of SG provisional application No. 10201706788W, filed 18 Aug. 2017, the contents of it being hereby incorporated by reference in its entirety for all purposes.

FIELD OF THE INVENTION

The present invention relates generally to the field of molecular biology and computational biology. In particular, the present invention relates to a method to identify and monitor protein-protein interactions directly in cells and tissues.

BACKGROUND OF THE INVENTION

A living cell arises from a myriad of biomolecule interactions occurring in time and space among proteins with nucleic acids, metabolites and lipids. Central to this intricate biological network are protein complexes that mediate the biochemical processes and the structural organization of the cell. They assemble and dissociate dynamically according to cellular needs, and are enriched in proteins implicated in genetic and infection diseases.

Proteins can interact with each other under different physical, cellular or physiological states and conditions to form protein complexes. These interactions are complex and dynamic, wherein the proteins and protein complex can assemble or dissociate according to the needs of the cell. It is crucial to be able to make live observations and study these interactions on a proteome-wide level in a cell so as to have a better understanding of these complex interactions during the physiological states. Such methods are much needed, as they would alleviate the current gap in understanding the complexities of dynamic protein interactions, which can be used to identify protein complexes that are modulated in diseases.

Large-scale endeavours have been embarked to populate the repertoire of plausible human protein complexes using specific cell lines. Data from these works and others, complemented by focused efforts, have amassed into a large protein-protein interaction network depicting the plausible cellular wiring and functional organization of the human proteome. However, the conservation of the assembled protein network and identified protein complexes across cell type, physiological states and diseased conditions is unclear.

There is a need to provide methods that permit efficient, system-wide monitoring and hypothesis-free identification of the formation and dynamics of protein-protein interactions and protein complexes directly in cells and tissues.

SUMMARY

In one aspect, the present invention refers to a method for identifying a protein interaction between one or more first proteins and one or more further proteins, said method comprising the steps of:
a) exposing one or more samples comprising the one or more first proteins and said one or more further proteins to at least one preselected condition for at least one preselected duration;
b) isolating and separating at least one soluble fraction from an insoluble fraction of said one or more samples; and
c) analysing the at least one soluble fraction or the insoluble fraction of step b) to identify said protein interaction between one or more first proteins and one or more further proteins in said one or more samples.

In another aspect, the present invention refers to the use of the method as described herein for screening for therapeutic drug targets, disease progression prognosis, determining efficacy of drug therapies, determining protein stoichiometry, identifying novel protein pathways, mapping protein interactomes, predicting protein function or mapping temporal protein interactions.

Definitions

The following words and terms used herein shall have the meaning indicated:

"Protein" refers to a polymer of amino acid residues, wherein a protein may be a single molecule or may be a multi-molecular complex. The term, as used herein, can refer to a subunit in a multi-molecular complex, polypeptides, peptides, oligopeptides, of any size, structure, or function. It is generally understood that a peptide can be 2 to 100 amino acids in length, whereas a polypeptide can be more than 100 amino acids in length. A protein may also be a fragment of a naturally occurring protein or peptide. The term protein may also apply to amino acid polymers in which one or more amino acid residues is an artificial chemical analogue of a corresponding naturally occurring amino acid. A protein can be wild-type, recombinant, naturally occurring, or synthetic and may constitute all or part of a naturally-occurring, or non-naturally occurring polypeptide. The subunits and the protein of the protein complex can be the same or different. A protein can also be functional or non-functional.

"Protein interaction" or "protein-protein interaction" refer to the association between two or more proteins. Protein-protein interaction may effect a change in properties or function of the individual proteins. Protein interactions may also elicit a biological effect in a cell or living organism. Protein interactions may be stable or transient. Each of these interactions may be strong or weak. It is generally understood that the strength and specificity of protein interactions are affected by properties such as, but are not limited to, protein structure, protein domains, concentration of proteins, thermal stability, solubility, temperature, mass, pH, density, volume, molecular bonds, electrical charge, chemical stability, viscosity, melting point, boiling point, or any combinations thereof. Stronger protein interaction can be achieved by covalent bonds such as disulphide bonds or electron sharing, whereas weaker protein interaction can be established by non-covalent bonds such as hydrogen bonds, Van der Waals forces, hydrophobic bonds or ionic interactions.

"Sample" refers to a specimen taken, obtained or derived from an organism. The sample can be obtained or derived from any multicellular or unicellular organism such as, but is not limited to, animal, plant, fungi, bacteria, archaea, virus or protist.

"Precipitation" refers to the co-aggregation of interacting proteins upon denaturation. Denaturation can be induced by one or more ways, for example, heat, chemical, radiation, pH, sonication, or any combinations thereof.

Proteins unfold and aggregate or precipitate upon denaturation. Interacting proteins can co-aggregate upon denaturation. Proteins that aggregate or precipitate are insoluble, are detectable in the insoluble fraction and are not detectable in the soluble fraction. When exposed to a range of conditions for varying durations, different proteins aggregate at different conditions. The percentage of protein that aggregate or remain soluble when a protein is exposed to different conditions for varying durations can be measured and the solubility of the protein at a range of conditions can be expressed in the form of a curve.

As used herein, "solubility" with respect to a protein refers to the solubility of a protein under different conditions. Proteins unfold and aggregate or precipitate upon denaturation. Interacting proteins can co-aggregate upon denaturation. The percentage of protein that aggregate or remain soluble when a protein is exposed to different conditions for varying durations can be measured and the solubility of the protein at a range of conditions can be expressed in the form of a solubility curve. For example, when exposed to a range of temperatures for varying durations, different proteins aggregate at different temperatures. The percentage of protein that aggregate or remain soluble when a protein is exposed to different temperatures for varying durations (thermal solubility (TS)) can be measured and the thermal solubility of the protein at a range of temperatures can be expressed in the form of a melt curve.

As used herein, "solubility curve" refers to the analysis or assessment of protein unfolding and co-aggregation events. The terms "melt curve" or "melting curve" refer to the analysis or assessment of protein unfolding and co-aggregation events when heat is the used to denature the protein.

"Proximity co-aggregation (PCA)" is a measure of the co-aggregation of proteins upon denaturation under different conditions. Interacting proteins co-aggregate upon denaturation, leading to similar solubility across different conditions. PCA can be used for system-wide intracellular study and monitoring of protein complex dynamics, wherein interacting proteins co-aggregate upon denaturation, leading to similar solubility across different conditions.

"Proximity co-aggregation (PCA) signature" refers to the pattern of protein interactions identified using PCA. PCA signature positively correlates with interaction stoichiometry and abundance stoichiometry, wherein the term "interaction stoichiometry" as used herein refers to the optimal degree of interaction between proteins, and "abundance stoichiometry" refers to the ratio between abundance of interacting proteins.

"Distance metric" refers to a measurement of distance between two data points. Distance metric may be used to measure similarity between two solubility curves or melt curves.

BRIEF DESCRIPTION OF THE DRAWINGS

The invention will be better understood with reference to the detailed description when considered in conjunction with the non-limiting examples and the accompanying drawings, in which.

DETAILED DESCRIPTION

In a first aspect, the present invention refers to a method for identifying a protein interaction between one or more first proteins and one or more further proteins, said method comprising the steps of:
a) exposing one or more samples comprising the one or more first proteins and said one or more further proteins to at least one preselected condition for at least one preselected duration;
b) isolating and separating at least one soluble fraction from an insoluble fraction of said one or more samples; and
c) analysing the at least one soluble fraction or the insoluble fraction of step b) to identify said protein interaction between one or more first proteins and one or more further proteins in said one or more samples.

A sample comprising one or more first proteins and one or more further proteins may be exposed to at least one preselected condition. The preselected condition is capable of causing a change in precipitation of the first protein when interacting with one or more further proteins compared to the first protein when not interacting with one or more further proteins. In one example, a change in precipitation may be an enhancement or reduction of precipitation. In another example, the preselected condition is capable of causing precipitation of the first protein when interacting with one or more further proteins compared to the first protein when not interacting with one or more further proteins.

Figure 3:
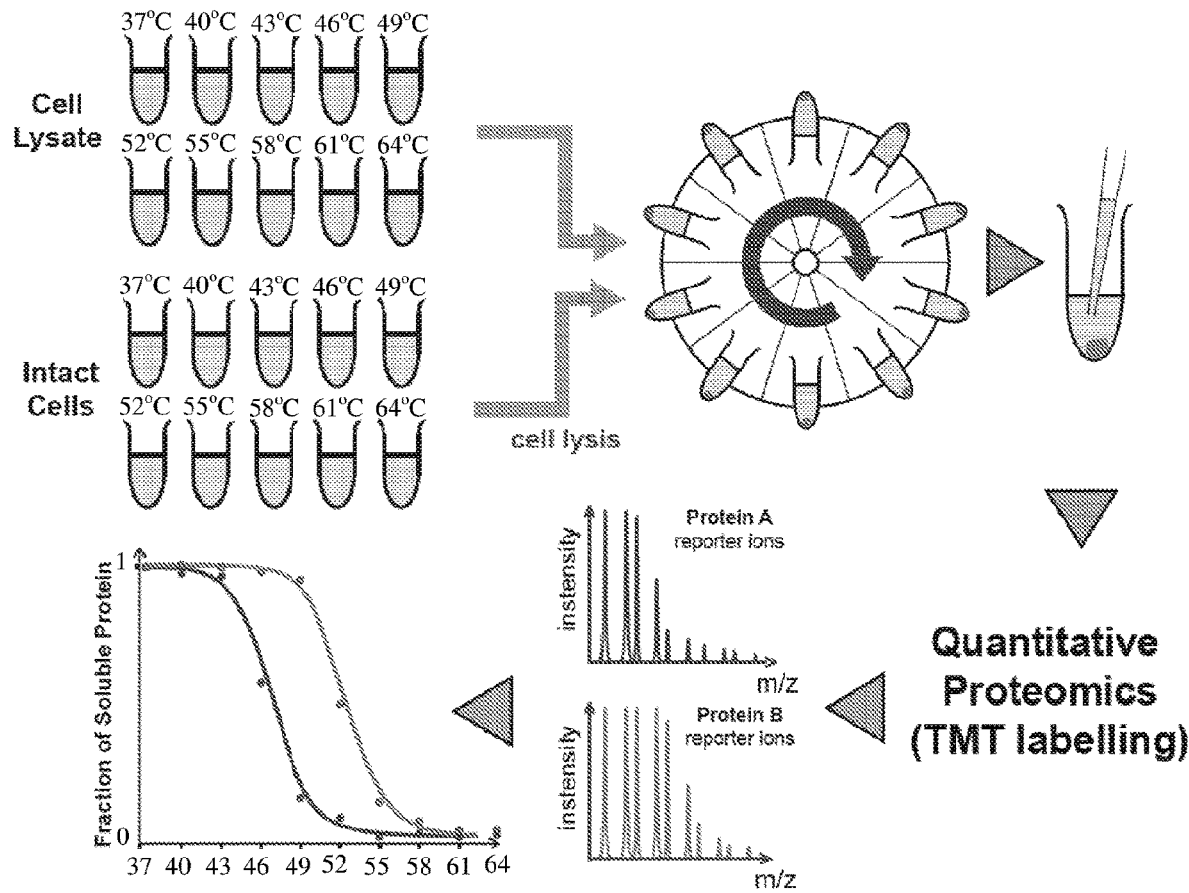
FIG. 3 shows a schematic that shows an overview of the MS-CETSA experiment. m/z, mass/charge ratio; TMT, tandem mass tags.

In one embodiment, the at least one preselected condition in step a) may be temperature, pH, concentration, chemicals (e.g. urea), radiation (e.g. microwave), sonication or any combinations thereof. In a preferred embodiment, the preselected condition is temperature or temperature range. It will generally be understood that a range of temperatures may be used in the present invention. For example, the temperature may be from about 30° C. to about 70° C. For example, from about 31° C. to about 69° C., about 32° C. to about 68° C., about 33° C. to about 67° C., about 34° C. to about 66° C., about 35° C. to about 65° C., about 36° C. to about 64° C., about 37° C. to about 63° C., about 38° C. to about 62° C., about 39° C. to about 61° C., about 40° C. to about 60° C., about 41° C. to about 59° C., about 42° C. to about 58° C., about 43° C. to about 57° C., about 44° C. to about 56° C., about 45° C. to about 55° C., about 46° C. to about 54° C., about 47° C. to about 53° C., about 48° C. to about 52° C., or about 49° C. to about 51° C. In another embodiment, the temperature may be from about 37° C. to about 64° C. In another embodiment, the preselected condition comprises preselected temperature of about 37.0° C., about 38.0° C., about 39.0° C., about 40.0° C., about 41.0° C., about 42.0° C., about 43.0° C., about 44.0° C., about 45.0° C., about 46.0° C., about 47.0° C., about 48.0° C., about 49.0° C., about 50.0° C., about 51.0° C., about 52.0° C., about 53.0° C., about 54.0° C., about 55.0° C., about 56.0° C., about 57.0° C., about 58.0° C., about 59.0° C., about 60.0° C., about 61.0° C., about 62.0° C., about 63.0° C., and about 64.0° C. In one example, the preselected condition is preselected temperature of, 37.0° C., 40.0° C., 43.0° C., 46.0° C., 49.0° C., 52.0° C., 55.0° C., 58.0° C., 61.0° C., and 64.0° C., as shown for example in FIG. 3.

The sample comprising one or more first proteins and one or more further proteins may be exposed to the at least one preselected condition for at preselected duration. The preselected duration can be in seconds (s), minutes (min), hours (hr) or days. For example, the preselected duration can be 10 s to 2 min, 1 min to 3 min, 2 min to 4 min, 3 min to 5 min, 4 min to 6 min, 5 min to 7 min, 6 min to 8 min, 7 min to 9 min, or 8 min to 10 min. In another example, the preselected duration can be 1 min, 2 min, 3 min, 4 min, 5 min, 6 min, 7 min, 8 min, 9 min or 10 min. In another example, the preselected duration is 3 min.

In one embodiment, the sample may be a biological sample. For example, the sample can be, but is not limited to, whole blood or a component thereof (e.g. plasma, serum), urine, saliva lymph, bile fluid, sputum, tears, cerebrospinal fluid, bronchoalveolar lavage fluid, synovial fluid, semen, ascitic tumour fluid, breast milk, pus, amniotic fluid, buccal smear, cultured cells, culture medium collected from cultured cells, cell pellet, a lysate, homogenate or extract prepared from a whole organism or a subset of its tissues, cells or component parts, or a fraction or portion thereof. In one example, the sample can be cells isolated from an organ from an organism, wherein the organ can be, but is not limited to, liver, brain, heart, spleen, kidney, bone, lymph nodes, muscles, blood vessels, bone marrow, pancreas, intestines, urinary bladder, or skin.

In another embodiment, the biological sample can be cultured cells from cell lines such as, but not limited to, HCT116, A375, MCF7, HEK293T, K562, HL60, HEK 293FT, HEK293, Hela, SF9, CHOs, Jurkat, Saos-2 or PC3. In yet another embodiment, the sample can be an intact cell or a cell lysate. In a preferred embodiment, the sample is an intact cell.

In one embodiment, the one or more samples can be obtained from the same sample or different samples. For example, the one or more samples can be one or more intact cells or cell lysates of the same cell line or cell type. In another example, the one or more sample can be one or more intact cells or cell lysates from two or more different cell lines or cell types.

In another embodiment, the samples can modified, wherein the modification comprises purification, dilution, alteration of pH, addition or removal of a salt, addition of an additive, addition of a drug or drug lead, oxidation or reduction, exposure to a chemical or compound, alteration of a cellular or physiological state, or alteration of a cellular environment. In one example, the sample can be modified by transfection using, but not limited to, plasmids, or nucleic acids, wherein the plasmids comprise sequence coding for a tag such as, but is not limited to GFP, HA, FLAG, mCherry, V5, GST, biotin, phosphate, histidine, streptavidin, or any combinations thereof. In another example, the sample can be modified by undergoing desalting, buffer exchange, gel filtration chromatography, size exclusion chromatography, or any combinations thereof. In yet another example, a cell lysate such as a K562 cell lysate may be desalted to deplete low-molecular weight (LMW) ligands so as to perturb complexes en masse and obtain MS-CETSA data for PCA validation. The sample can also be modified by exposure to chemicals including, but not limited to, methotrexate, Dimethyl sulfoxide (DMSO), or tumour necrosis factor alpha (TNFα), or any combinations thereof.

The first and/or further protein can be interacting proteins, proteins in a protein complex, or subunits in a protein complex. In one preferred embodiment, first and/or further protein may be wild-type or recombinant proteins. In one example, the first protein is V5 tagged cyclin E1 that was identified and detected by protein A agarose beads pre-coupled to V5 tag antibodies, and the further protein is Cdk2. In another example, the first protein can be 40S or 60S ribosomal subcomplex, and the further protein can be 40S or 60S ribosomal subcomplex, wherein it is generally known in the art that 40S and 60S ribosomal subcomplexes form the ribosomal complex.

The first and further proteins can be from the same or from different samples. The first and further proteins can also be from the same or from different sections of the samples. In one example, the first and further proteins can be within the cell lysate. In another example, the first and further proteins can be within or on the cell.

The one or more samples may comprise a soluble fraction and an insoluble fraction. Proteins unfold and aggregate or precipitate upon denaturation and are insoluble. Aggregated proteins are detectable in the insoluble fraction. Proteins that are not unfolded or in the native form are detectable in the soluble fraction.

The soluble fraction of the one or more samples from step a) can be isolated and separated from the insoluble fraction. Prior to the step of isolating and separating the fractions from the samples, the sample can be treated using methods such as, but not limited to, freeze-thaw, mechanical shearing, sonication, centrifuging, filtering, or any combinations thereof. Isolating and separating the soluble fraction from the insoluble fraction can then be accomplished by conventional methods known in the art, examples include, but are not limited to, pipetting the soluble fraction, pouring out the soluble fraction, or any combinations thereof.

In one embodiment, the samples or cells may be lysed to obtain a cell lysate prior to isolating and separating the at least one soluble fraction from the insoluble fraction. In a further embodiment, the cell lysate may be centrifuged or filtered to obtain a supernatant fraction prior to isolating and separating the at least one soluble fraction from an insoluble fraction.

In some embodiments, the sample or cells may be lysed by two free-thaw cycles and mechanical shearing, wherein the supernatant was separated from the cell debris and aggregated protein pellet by centrifugation using conditions generally known in the art.

The at least one soluble fraction or the insoluble fraction of step b) may then be analysed to identify the protein interaction between one or more first proteins and one or more further proteins in the sample.

In one example, analysis can be done by a computational method. In another example, analysis can be done by a computational method that comprises computational algorithms. In yet another example, analysis can be done by a computational method that comprises computational algorithms to deconvolute the data to identify protein complexes or protein-protein interactions present or modulated.

In one embodiment, the analysis in step c) may further comprise the steps of: i) determining the solubility of the proteins; and ii) obtaining a proximity co-aggregation (PCA) signature to identify said protein interaction between one or more first proteins and one or more further proteins in said one or more samples.

Solubility can be determined by conventional methods used to study proteins and protein complexes, including methods for include capture of proteins and/or protein binding partners, detection of proteins and/or protein binding partners, identification of proteins and/or protein binding partners, testing thermal stability or any combinations thereof. For example, methods to capture proteins and/or protein binding partners include, but not limited to, affinity purification, immunoprecipitation, co-immunoprecipitation, chromatin immunoprecipitation, ribonucleoproteins immunoprecipitation, or any combinations thereof, have been used to precipitate proteins and protein complexes. Methods to detect proteins and/or protein binding partners can include, but is not limited to, immunodetection assays, fluorescence assays, immunostaining, colorimetric protein assays, or any combinations thereof. Identification of proteins and/or protein binding partners can be done by mass spectrometry (MS), and its variations such as tandem MS, thermal-ionization MS, MALDI-TOF, or accelerator MS. Methods to determine thermal stability of proteins are conventional and known in the art, and can include, but is not limited to, thermal shift assay, DSF-GTP technique, thermofluor assay, intrinsic tryptophan fluorescence lifetime assay, intrinsic tryptophan fluorescence wavelength assay, static light scattering assay, fast parallel proteolysis (FastPP) assay, size exclusion chromatography (SEC-TS), fluorescence-detection size exclusion chromatography (FSEC-TS), radioligand binding thermostability assay, or combinations thereof. Recently, cellular thermal shift assay (CETSA) has been discovered as a method to quantify ligand-induced thermal stabilization of proteins. Even more recently, MS is used for multiplexed quantification with CETSA in a new method known as mass spectrometry-cellular thermal shift assay (MS-CETSA), also known as thermal proteome profiling (TPP). MS-CETSA allows a proteome-wide assessment of protein-ligand binding by quantifying the thermal stability of proteins, wherein MS-CETSA data is usually presented in the form of a melting curve. In one example, solubility can be determined by, but not limited to, MS-CETSA, MS, CETSA, immunoprecipitation, co-immunoprecipitation, or any combinations thereof. In one preferred embodiment, solubility is obtained by mass spectrometry. In another example, solubility can be determined by MS-CETSA using control samples without exogenous ligands. In one example, solubility is determined by a computational method, wherein the soluble portion of each protein in each sample relative to a reference sample is computed by dividing its MS readings to that of the reference sample. The computed value is denoted as $TS_t^d(x)$ which is the solubility of protein x at temperature d after time t.

In one embodiment, the solubility of the one or more first proteins may be compared to the solubility of the one or more further proteins in said one or more samples and the similarity in solubility between the one or more first proteins and one or more further proteins in said one or more samples may be determined to obtain the PCA signature, wherein a non-random increase in similarity in solubility is indicative of a protein interaction between said one or more first proteins and said one or more further proteins in said one or more samples. In one example, the non-random increase in similarity in solubility has a P-value<0.05. It will generally be understood that the lower the P-value, the less likely the increase in similarity in solubility is random.

Determining the similarity in solubility comprises comparing the solubility of the one or more first proteins and the one or more further proteins to a reference. The reference used to determine the similarity in solubility can the solubility similarity of a group of proteins. In one embodiment, the reference is the solubility similarity of a random group of proteins in the same sample or in a different sample. In another embodiment, the reference is the solubility similarity of the one or more first protein and one or more further proteins in a different sample. In one example, the reference is a protein complex from the CORUM database. In another embodiment, the reference can be predicted or inferred protein complex.

The PCA signature is obtained by computational approaches, wherein data that comprises parameters such as, but is not limited to, temperature, unfolding event, co-aggregation event, solubility curve, melting curve, solubility, time, or any combinations thereof, are used to derive the PCA signature. This can include the use of different algorithms, wherein the algorithms can include machine learning classifiers or be scored without training dataset. In one example, the PCA signature is obtained by scoring known protein-protein interaction data and using existing network clustering algorithms to identify known and putative protein complexes. In another example, the PCA signature is obtained by weighting each interacting protein pairs in an assembled protein-protein interaction network with PCA-derived scores and assessing their capacity to assist network/graph clustering algorithms such as, but not limited to, CMC, ClusterOne, MCL, or any combinations thereof, to identify protein complexes annotated in CORUM. In yet another example, the PCA signature is obtained by using machine learning classifiers to integrate multiple orthogonal data and calibrated for optimal result with gold standards like CORUM and STRING. In yet another example, the PCA signature is obtained by scoring each interacting protein pairs solely using PCA without training datasets or gold standards for calibration. In yet another example, the PCA signature is obtained by using other network/graph clustering algorithms such as, but not limited to, Coach, IPCA, or any others that accept unweighted network as input, and subsequently ranked the predicted complexes according to their weighted density. In yet another example, the PCA signature is obtained by PCA-based scoring of protein complexes predicted by COACH.

In one embodiment, similarity in solubility between the one or more first proteins and one or more further proteins may be determined using the average distance between the solubility of the one or more first proteins and one or more further proteins. It will be understood that average distance may be measured at one or more temperatures or data points. The average distance may be determined using one or more distance metrics and the use of said distance as an inverse measure of solubility similarity between a putative interacting protein and non-interacting protein. In one example, distance metric can comprise, but is not limited to, Euclidean distance, Pearson's correlation coefficient, cosine similarity, Manhattan distance, Minkowski distance, Jaccard similarity, Mahalanobis distance, or Chebyshev distance. In one preferred embodiment, the distance metric is Euclidean distance or Pearson's correlation coefficient. In one example, the similarity in solubility at every or subset of temperature d and time t for pairs of protein is then computed with metrics like Euclidean distance or Pearson's correlation coefficient. This similarity in solubility across every or subset of temperature d and time t between protein x and y is denoted as $E(TS)_{x,y}$. The computed value correlates with probability of interaction and interaction stoichiometry (portion of protein interacting with each other). The distributions of solubility similarity E(TS) among known interacting protein pairs and non-interacting protein pairs are derived to compute the probability that two proteins are interacting based on their solubility similarity. In another example, for each known or predicted protein complexes, including binary protein-protein interactions, the E(TS) of every subunit pairs of the complex are determined as described. For protein complexes with more than two subunits, the difference in computed solubility similarity among subunit pairs permits differentiating subunit pairs or sub-complex with potentially higher or lower interaction/abundance stoichiometry. The difference in solubility similarity, denoted as F, is computed as $|E(TS)_{x1,y1} - E(TS)_{x2,y2}|$ for protein pair x1 x2 and protein pair y1 and y2. Statistical significant of F computed in v is assessed by deriving the distribution of difference in solubility similarity between two protein pairs that are randomly selected. Empirical P-value is computed as the frequency in which randomly selected protein pairs have equal or higher F value compared to actual subunit pairs. The average and standard deviation of E(TS) among all subunit pairs for each complex, denoted as A and SD respectively, can be computed. In yet another example, to identify differentially modulated protein complexes across different biological samples/conditions (that have been heated with different temperature for different duration), the difference in A and SD computed for the same complex between two biological samples or conditions are derived. The difference is denoted as $D(A)_{i,j}$ and $D(SD)_{i,j}$ for biological sample/condition i and j. Statistical significance of $D(A)_{i,j}$ and $D(SD)_{i,j}$ is estimated by randomly sampling n proteins where n is the number of subunits of the protein complex with solubility data across the two biological sample/conditions. The $D(A)_{i,j}$ and $D(SD)_{i,j}$ of the randomly selected proteins are computed. Empirical P-value is computed as the frequency in which randomly selected protein set have equal or higher $D(A)_{i,j}$ and $D(SD)_{i,j}$ than the actual protein complex.

In a second aspect, the present invention refers to the use of the method according the present invention for screening for therapeutic drug targets, disease progression prognosis, determining efficacy of drug therapies, determining protein stoichiometry, identifying novel protein pathways, mapping protein interactomes, predicting protein function or mapping temporal protein interactions. The method as disclosed herein can be used in various ways. In one example, the method can be used in the areas of, but not limited to, biology, chemistry, physics, molecular biology, cell biology, proteomics, immunology, pharmacology, structure biology, biophysics, or biochemistry. In another example, the method can be used for, but not limited to, drug screening, screening for therapeutic drug targets, disease progression prognosis, determining efficacy of drug therapies, determining protein stoichiometry, identifying novel protein pathways, mapping protein interactomes, predicting protein function, mapping temporal protein interactions, intracellular studies of weak or transient protein-protein interactions that are not preserved in lysate, validate protein complexes, or study the chemical modulators of protein complexes and interactions directly in non-engineered cells.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

As used in this application, the singular form "a," "an," and "the" include plural references unless the context clearly dictates otherwise. For example, the term "a genetic marker" includes a plurality of genetic markers, including mixtures and combinations thereof.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention and comparative examples will be further described in greater detail by reference to specific Examples, which should not be construed as in any way limiting the scope of the invention.

MATERIALS AND METHODS

Cdk2 and Cyclin E1 Experiments

Cells Transfection

2×106 HEK 293FT cells were transfected by the calcium phosphate method during 8 hours with a total of 12 μg of plasmids encoding human V5 tagged cyclin E1 (pBobi-hscyclinE1-V5-PKB057) and/or HA-tagged Cdk2 (pCMV-hsCdk2-HA-PKB407) and/or mCherry (pBobi-mCherry-PKB1847). Cells were harvested after 48 hours by scrapping the cells in PBS, before counting those and aliquoting for intact cell CETSA experiment.

Western Blotting and Immunodetection 10 or 25 μg of protein extracts from transfected 293T cells were separated on 9% polyacrylamide gels, transferred onto polyvinylidene difluoride membranes (PVDF, Millipore, #IPVH0010) using a semi-dry system and blocked in Tris-buffered saline (TBS) with 0.1% Tween20 and 4% non-fat dry milk (Bio-Rad, #1706404). Blots were probed with the appropriate primary antibodies overnight at 4° C. (anti-V5, Invitrogen #R960-25; anti-HA, Rabbit polyclonal antisera against HA were raised using an HA epitope as antigen, followed by secondary goat anti-mouse (Pierce, #0031432) or anti-rabbit antibodies (Pierce, #0031462) conjugated to horseradish peroxidase and developed using enhanced chemiluminescence (PerkinElmer, #NEL105001EA).

Immunoprecipitations were performed with minor modifications. Briefly, 50 μg of protein extract from transfected 293T cells were incubated with protein A agarose beads (Invitrogen #15918-014) pre-coupled to antibodies directed against V5 tag (Invitrogen #R960-25) or HA tag (as described above) for 5 hours at 4° C. in EBN buffer (80 mM β-glycerophosphate pH 7.3, 20 mM EGTA, 15 mM $MgCl_2$, 150 mM NaCl, 0.5% NP-40, 1 mM DTT, and protease inhibitors [20 μg/ml each of leupeptin, chymostatin, and pepstatin (Chemicon, EI8, EI6 and EI10)]). After incubation, beads were washed three times in EBN buffer, dried and resuspended in laemmli buffer 1× concentrated and the supernatant were ready for electrophoresis separation on polyacrylamide gel.

CETSA and Desalting Experiment

For intact cell CETSA experiments, the cells were harvested, washed 34 and resuspended in PBS. Liver from a C57BL/6 mouse was perfused via the portal vein with PBS immediately after sacrificing. The perfused liver was collected and the tissue was passed through a 65μ cell strainer with cRPMI to obtain a single cell suspension. The single cell suspension was then washed once with PBS and then resuspended in PBS to obtain a cell concentration of 40 million cells/mL. Cells from cell lines or mouse liver were then divided into 10 aliquots, heated from 37° C. to 64° C. at 3° C. interval for 3 min in a 96-well thermocycler, followed by 3 min at 4° C. The cells were lysed post-heat treatment by the addition of 2× kinase buffer (100 mM HEPES, pH 7.5, 10 mM beta-glycerophosphate, 0.2 mM sodium orthovanadate ($Na_3VO_4$), 20 mM $MgCl_2$, 4 mM TCEP, 2× protease inhibitor cocktail), followed by the two freeze-thaw cycles with liquid nitrogen and mechanical shearing with the syringe and a final freeze thaw cycle. The cell debris and aggregated protein pellet was removed by centrifugation at 20,000 g for 20 min at 4° C. The supernatant was then used for mass spectrometry sample preparation. For lysate CETSA experiment, 1 mL of K562 lysate is first generated from 40 million cells of K562 with 1× kinase lysis buffer containing 50 mM HEPES with pH 7.5 at 4° C., 5 mM β-glycerophosphate, 0.1 mM activated sodium orthovanadate, 10 mM magnesium chloride, 2 mM TCEP, and EDTA-free protease inhibitor. The cells were lysed completely with 2× freeze thaw followed by 10× mechanical shearing with 21" gauge needle, 3× with 30" gauge needle, and a final freeze thaw. Lysate were spun down at 20,000 g for 20 minutes at 4° C. The supernatant is retained, aliquoted and frozen and stored at −80° C. Aliquots are completely thawed at and to room temperature prior to CETSA heating experiment.

Desalting of K562 Lysate

PD-10 desalting columns (GE Healthcare, Product number: 17-0851-01) were equilibrated using 1× kinase lysis buffer. Subsequently, 1 mL of K562 lysate was added to PD-10 column, it is followed by topping up with 1.5 mL of 1× kinase lysis buffer. Next, the elution step was carried out with 0.5 mL of 1× kinase lysis buffer for seven times. Two of the seven fractions with the highest protein concentration were used and combined to give 1 mL of desalted lysate for CETSA experiments.

Methotrexate and S-Phase Experiment

K562 were plated at $0.25 \times 10^6$ cells/mL and treated for 48 hours with either vehicle (DMSO) or 20 μM methotrexate (Sigma) dissolved in DMSO. Cells were harvested, washed, resuspended in ice-cold PBS buffer, and subsequently aliquoted into 10 fractions. Standard intact cell CETSA and lysis protocol followed.

NFκB and Methotrexate Experiments

Western Blotting

Cells were harvested after 48 hours of methotrexate (20 μM) and/or 30 minutes of TNF-α (10 ng/mL) treatment. Cells were washed with DPBS (without calcium and magnesium) once, then lysed in TOTEX Buffer (20 mM Hepes at pH 7.9, 0.35M NaCl, 20% Glycerol, 1% NP-40, 1 mM $MgCl_2$, 0.1 mM EGTA) including 50 mM NaF, 0.3 mM $Na_2VO_3$ and protease inhibitor cocktail. Supernatant including proteins was collected, followed by centrifugation at full speed for 20 minutes. Western blotting was performed by following standard procedures using the following antibodies: Rabbit Anti-phospho-IKKα/β (S180/181) (1:1,000; Bioworld Technology, BS5082), Rabbit Anti-phospho-IKBα (S32) (1:1,000; Cell Signalling Technology, 2859), Rabbit Anti-IKBα (1:1,000; Santa Cruz Biotechnology, sc-371), Rabbit Anti-phospho-p65 (S536) (1:1,000; Cell Signalling Technology, 3031), Mouse Anti-HSP90 (1:1,000; BD, 610419), Goat Anti-Rabbit IgG-HRP (1:5,000; Santa Cruz Biotechnology, sc-2054) and Goat Anti-Mouse IgG-HRP (1:5,000; Santa Cruz Biotechnology, sc-2005).

Co-Immunoprecipitation

Harvested cells were lysed in Immunoprecipitation lysis buffer (50 mM Tris at pH 8.0, 1% Triton X-100, 0.5% NP-40, 170 mM NaCl, 5% Glycerol, 1% EDTA) including protease inhibitor cocktail and sonicated for 5 minutes (30 seconds ON, 30 seconds OFF). Supernatant including proteins was collected after centrifugation and protein concentration was measured. 1 mg protein of each sample was used for immunoprecipitation. Samples were incubated with PureProteome Protein A Magnetic beads (Millipore, LSK-MAGA10) for 1 hour to pre-clear, then beads were removed and samples incubated with antibodies: Rabbit Anti-NF-κB p65 (5 μg/mg sample; Santa Cruz, sc-372), Rabbit Anti-Anti-NF-κB p50 (5 μg/mg sample; Santa Cruz, sc-7178) and Normal Rabbit IgG (5 μg/mg sample; Santa Cruz, sc-2027) for overnight. After incubation, beads were added to capture antibody-protein complexes for 1 hour, and then proteins were eluted from beads using SDS loading buffer. Samples were used for western blotting using following antibodies: Rabbit Anti-IKBα (1:1,000; Santa Cruz Biotechnology, sc-371), Rabbit Anti-NF-κB p65 (1:1,000; Santa Cruz, sc-372), Rabbit Anti-NF-κB p50 (1:1,000; Santa Cruz, sc-7178) and Veriblot Secondary Antibody (HRP) (1:10, 000; Abcam, ab131366).

Cell Culture

K562 and A375 were cultured in RPMI medium (Gibco, Product Number: A10491), HEK 293T and MCF7 were cultured in DMEM medium (Gibco, Product Number: 11995), HL60 was cultured in IMDM medium (Gibco, Product Number: 12440), and HCT116 was cultured in McCoy medium (Gibco, Product Number: 12330). All media are supplemented with 10% Fetal Bovine Serum (Biowest, Product Number: S1810) except IMDM medium which was supplemented with 20% Fetal Bovine Serum. RPMI and DMEM were further supplemented with L-Glutamine (Gibco, Product Number: 25030), Non-essential Amino Acid (Gibco, Product Number: 11140) and Penicillin Streptomycin (Gibco, Product Number: 15140). All adherent cell lines were passaged or harvested with Trypsin-EDTA (0.25%) phenol red (Gibco, Product Number: 25200).

MS Sample Preparation and Data Processing

Supernatant was collected after 10 or 20 mins centrifugation at 20,000 g, 4° C. and soluble protein quantified with BCA assay. Proteins were denatured in a solution of 0.1% (w/v) RapiGest™ SF Surfactant (Waters), reduced with 20 mM TCEP at 55° C. for 20 min and then alkylated with 55 mM chloroacetamide at room temperature for 30 min. The proteins were pre-digested with Lys-C (Wako) for 3-4 h at 37° C., followed by digestion with trypsin enzyme (Promega) for overnight at 37° C. The samples were brought down to pH 2 with 1% TFA to hydrolyse RapiGest™ and pelleted down by centrifugation. The digested samples were collected from supernatant and completely dried up in a vacuum concentrator (Eppendorf). The samples were then solubilized in 100 mM or 200 mM TEAB buffer (pH 8.5) and labelled with TMT10plex isobaric label reagent (Pierce) according to the manufacturer manual. The labelling reaction was carried out for 1-2 h at RT before being quenched with 1M Tris buffer (pH 7.4). The labelled samples were combined according to label set, acidified and desalted on C18 Sep-Pak cartridges (Waters). The desalted samples were dried, and re-suspended in 5% Ammonium hydroxide solution (pH 10.0) and then pre-fractionated into 80 fractions using a high pH reverse-phase Zorbax 300 Extend-C18 column (5 um, 4.6 mm×250 mm, 134 Agilent) on an ÄKTAmicro system (GE Healthcare). The pre-fractionated samples were concatenated into 20 injection fractions for each sample.

Each injection sample was separated on 50 cm×75 um EASY-Spray™ C18 LC column (Thermo Scientific) in a 80 min gradient of solvent A (0.5% acetic acid in water) and solvent B (80% ACN, 0.5% acetic acid in water) on an Dionex UltiMate 3000 RSLCnano system (Thermo Fisher Scientific), coupled with Q Exactive™ or Q Exactive™ HF mass spectrometer (Thermo Fisher Scientific). The data was acquired in a data-dependent-acquisition. Top 12 peaks in each MS scan were subject to higher energy collisional dissociation (HCD) fragmentation. MS1 scan resolution was 70,000 (at m/z=200 Th) and MS/MS scan resolution was 35,000.

Peak lists were generated using Thermo Proteome Discoverer software (version 2.0.0, Thermo Fisher Scientific). Spectra were searched using both Mascot and Sequest against target-decoy Human HHV4 Uniprot database. Carbamidomethyl cysteine and TMT10plex labelling on peptide N-terminus and Lysine were set as fixed modifications. Oxidated (M), Deamidated (NQ) and acetylated protein N-terminus were set as variable modifications. For peptide assignment, minimal length of 6 amino acids and maximum 3 missed cleavages was required, while allowing for maximum 30 ppm mass deviation for MS survey scan and 0.06 Da mass deviation for MS/MS ion fragments, respectively. FDR control was performed on both PSM and peptide level at the level of 0.01 for high and 0.05 for medium confidence peptides. The co-isolation threshold for reporter ion quantification was set at 50%. Protein groups were assembled for downstream data analysis.

MS Data Post-Processing and Bioinformatic Analysis

Data Normalization and Curve Fitting

Reporter ion intensity of each protein from each sample is divided by the reporter ion intensity of the same protein from the 37° C. sample (lysate or intact cell) to obtain normalized solubility of protein across different temperatures. These readings of every protein from each MS run is derived from the average reading of their isoforms (e.g. PXXXXX-1, PXXXXX-2) weighted according to ratio count (the number of PSMs used for quantification). The ratio count for computed average is computed as sum of ratio counts. UniProt accession of common contaminants and fragmented sequences are removed from proteins identified in MS run of each technical and biological replicates. Next, for each temperature, the median of median (MoM) solubility readings of protein across replicates is computed. The MoMs for the ten temperatures are then used to derive a sigmoidal curve fitted with a three-parameter log-logistic function (LL3.u where the upper limit is 1.0) using the drc (Analysis of Dose-Response Curves) R package. This sigmoidal curve can be interpreted as general solubility behaviour of the human proteome across different temperatures. It was assumed this general solubility is conserved across replicates, thus scale readings of each temperature of each replicate accordingly to exhibit this. Specifically, the solubility reading of every protein is adjusted by a fixed value for each sample and temperature such that the median reading at each temperature now fall onto the derived sigmoidal curve. To combine replicates for analysis, solubility readings of the same protein across replicates are averaged out weighted by ratio count which are summed up accordingly. The solubility values across the ten temperatures for each protein are individually fitted to a quartic function with R to derive a melting curve for visualization and inspection.

Empirical Statistical Assessment of PCA Signature

To identify known human protein complexes that exhibit PCA behaviour, for each protein complex, the average Euclidean distance was computed (denote as $E_{avg}$) between melting curves among all pairs of subunits of a protein complex. 10,000 random protein set of same protein number were randomly sampled and compute the $E_{avg}$ for each random set. The empirical P-value of observed $E_{avg}$ for a protein complex is then determined as frequency of random protein sets that generate $E_{avg}$ equal or smaller than the $E_{avg}$ of a protein complex. Specifically, let $PA=(p1, p2 \ldots, p_n)$ be the set of n unique subunits of protein complex A with solubility data. The average Euclidean distance among all unique subunit pairs ($E_{avg}$) from $P_A$ is computed as $$E_{avg}(P_A) = \left( \sum_{\substack{1 \leq x < n \\ x < y \leq n}} d(p_x, p_y) \right) / m \quad (1)$$

in which m, the number of unique subunit pairs from $P_A$, is equal to $(n^2-n)/2$, and $d(p_x, p_y)$, the Euclidean distance between melting curve of protein $p_x$ and $p_y$, is computed as $$d(p_x, p_y) = \sqrt{\sum_{i=1}^{10}(x_i - y_i)^2} \quad (2)$$

where $(x_1, x_2, x_3, x_4, x_5, x_6, x_7, x_8, x_9, x_{10})$ and $(y_1, y_2, y_3, y_4, y_5, y_6, y_7, y_8, y_9, y_{10})$ denote the normalized solubility of protein $p_x$ and $p_y$ at 37° C., 40° C., 43° C., 46° C., 49° C., 52° C., 55° C., 58° C., 61° C. and 64° C. respectively. To estimate probability of obtaining identical or smaller value than $E_{avg}$ ($P_A$), $E_{avg}$ was computed for 10,000 randomly selected protein set of size n. The empirical P-value for observed $E_{avg}$ ($P_A$) is determined as the frequency of random protein set that has $E_{avg} \leq E_{avg}$ ($P_A$).

Empirical Statistical Assessment of Observed PCA Signature Change

If $P_A=(p_1, p_2 \ldots, p_n)$ is the entire set of subunits from complex A with solubility data from both DMSO- and methotrexate-treated K562 samples, the difference is PCA signature is computed as $$\Delta_{(DMSO-MTX)} = E_{avg}(P_{A(DMSO)}) - E_{avg}(P_{A(MTX)}) \quad (3)$$

where $E_{avg}$ ($P_{A(DMSO)}$) and $E_{avg}$ ($P_{A(MTX)}$) is computed from solubility data derived from DMSO- and methotrexate-treated sample(s) respectively. To assess the statistical significance of observed $\Delta_{(DMSO-MTX)}$, $\Delta$ for 10,000 randomly selected protein set of size n were computed. Statistical significance of observed $\Delta_{(DMSO-MTX)}$ is then estimated as frequency of random protein set that result in $\Delta \leq \Delta_{(DMSO-MTX)}$.

Construction of Interaction Networks Weighted with PCA-Derived Z Scores

Weighted interaction network specific for each cell line were constructed. Every reported protein-protein interaction is weighted with cell-specific MS-CETSA data. First, a derivative of Euclidean distance, $E^x=1/(1+E)$, is computed for each reported protein-protein interaction where E is the Euclidean distance between melting curves of two interacting proteins (see equation 2). $E^x$ will be bounded between 0 and 1 with more symmetrical distribution. Next, a Z-score for each protein-protein interaction is derived as $(E^x-\mu)/\sigma$ where $\mu$ and $\sigma$ is the mean and standard deviation of $E^x$ computed from all pairs of protein identified in each cell line. This Z-score permits direct comparison of PCA signatures across cell lines. To facilitate identification of possibly differentiated protein-protein interactions in each cell line, a basal interaction network is constructed from averaging the Z-scores from the six cell lines, after removal of the highest and lowest Z-scores, for each protein-protein interaction.

Analysis of Interaction and Abundance Stoichiometry Between Proteins

Both interaction and abundance stoichiometry is normalized to the bait protein. For purpose of analysis, the stoichiometry is normalized to the higher abundant protein instead. Specifically, if interaction stoichiometry F or abundance stoichiometry A of an interacting protein is greater than 1, it is converted to 1/F or 1/A respectively.

Differential Protein Expression Analysis

The limma R package is used to identify differentially expressed proteins between DMSO and methotrexate-treated K562 cells from two sets of biological replicates. Supernatant samples from 37° C. treatment of original CETSA/TPCA experiment are processed for MS analysis as per described earlier with TMT isobaric label reagent (Pierce). Raw MS data are processed as described earlier. A scaling factor specific to sample x (denote as $SF^x$) is computed as $I^x/\min\{I^1, I^2, I^3, I^4\}$ where $x \in \{1, 2, 3, 4\}$ and $I^x$ is the total reporter ion intensity of all proteins for sample x. Subsequently, the reporter ion intensity for every protein in sample x is divided by $SF^x$. The data is then log-transformed and input as single channel data type to limma package, contrasting methotrexated-treated sample to DMSO-treated samples, and p-value adjusted by "fdr" for multiple hypothesis testing.

Example 1

Interacting Protein Pairs Exhibit Strong PCA Signature

Figure 1:
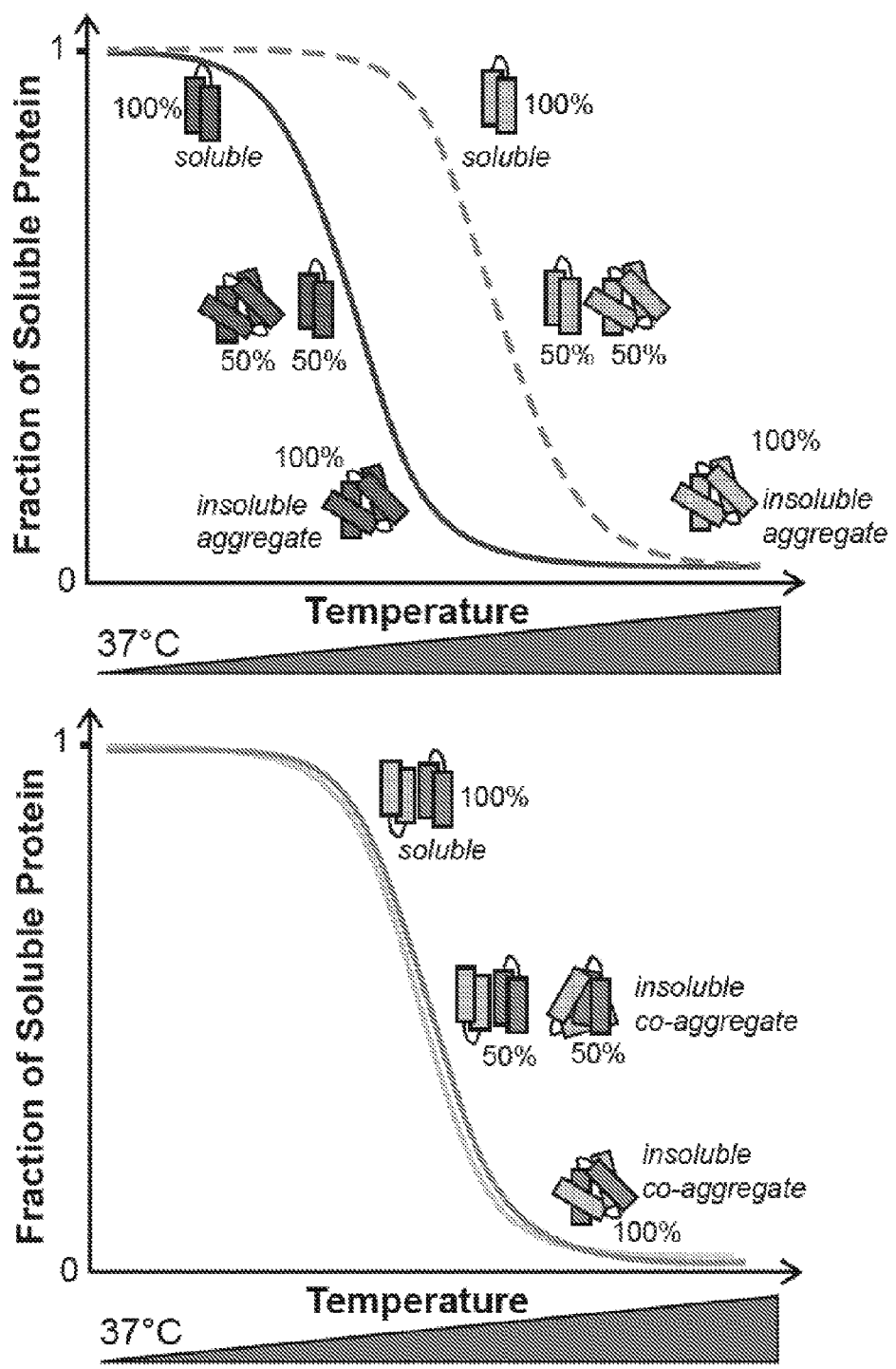
FIG. 1 shows a schematic that represents the principle of PCA for monitoring protein-protein interactions: Co-aggregation and precipitation among interacting proteins result in similar protein solubility across different denaturing temperatures. The graphs represent the fraction of soluble proteins of non-interacting proteins (left) and interacting proteins (right) at different temperature points.
Figure 2:
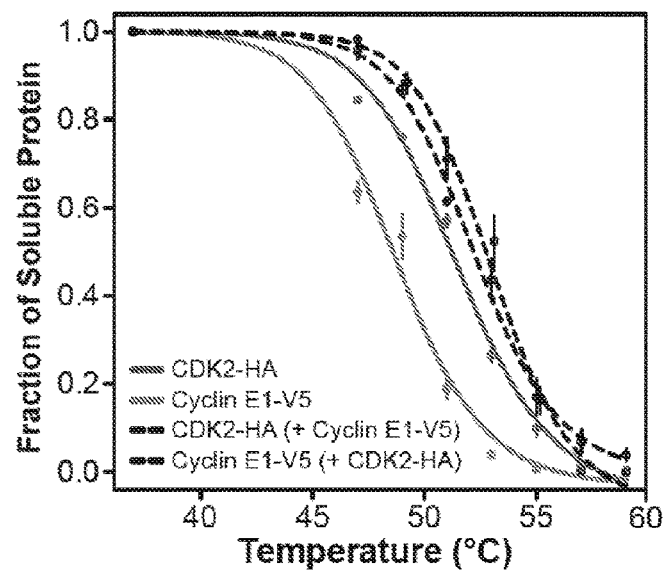
FIG. 2 shows scatter plots that represent the melting curves of CDK2-HA, Cyclin E1-V5, CDK2-HA (+Cyclin E1-V5) and Cyclin E1-V5 (+CDK2-HA). The cointeracting cyclin E1 and Cdk2 exhibit similar melting curves: HEK 293T cells were transfected with plasmids encoding V5-tagged cyclin E1 and/or HA-tagged Cdk2, followed by the intact cell CETSA experiment. Data are from immunoblots of three biological replicates (mean±SD) and are fitted with a three-parameter log-logistic function.
Figure 24:
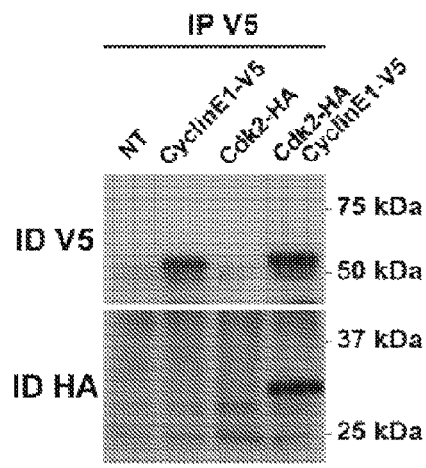
FIG. 24 shows photos of western blot analysis. (A) shows the assessment of co-immunoprecipitation of cyclin E1-V5 and Cdk2-HA. (B) shows the solubility of cyclin E1-V5 and Cdk2-HA at different temperature in the absence and presence of its interaction partner. Three biological replicates are performed and representative blots are showed.
Figure 24:
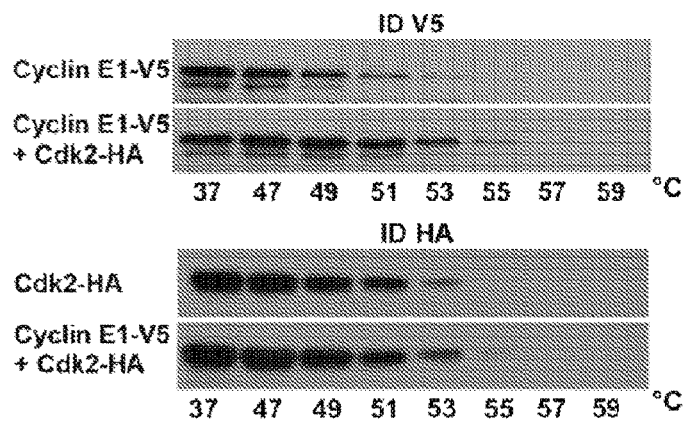

PCA was investigated with the well-characterized Cdk2-cyclin E1 complex, deriving the melting curves using immunoblots for both proteins overexpressed in human embryonic kidney (HEK) 293T cells (FIG. 24A and FIG. 24B). Individually expressed cyclin E1-EV5 and Cdk2-HA (hemagglutinin) display distinct melting curves, but they interact and are stabilized with similar melting curves when coexpressed (FIG. 2 and FIG. 24A), consistent with the PCA hypothesis.

Figure 4:
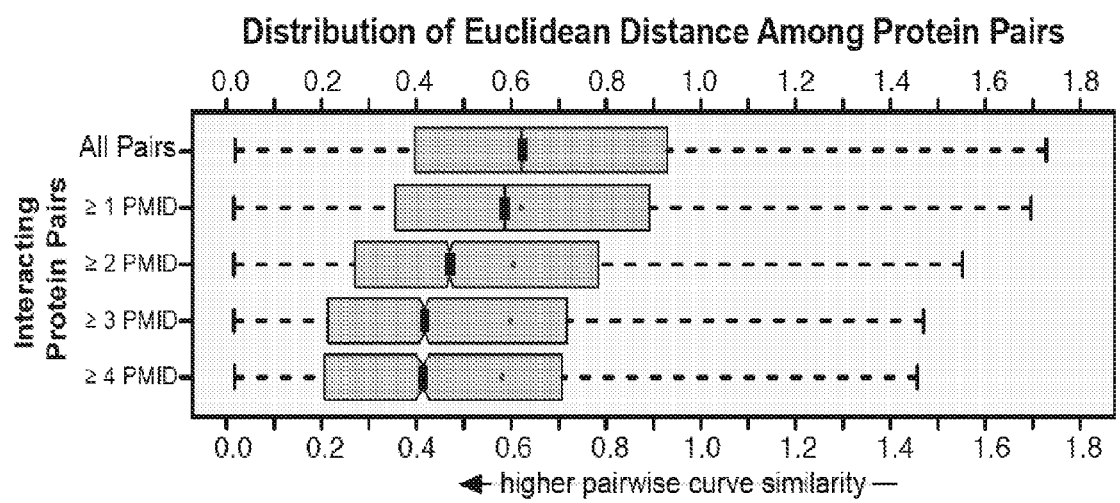
FIG. 4 shows 2 horizontal box plots that represent the distribution of melting curve similarities (based on Euclidean distance among protein pairs). (A) shows the distribution of melting curve similarities between known interacting protein pairs according to number of reporting publications: PMID, PubMed identifier. Dark grey dots indicate the median of all protein pairs of each respective protein subset. (B) shows a horizontal box plot that represents the distribution of melting curve similarities of known interacting protein pairs and interacting protein pairs in CORUM.
Figure 4:
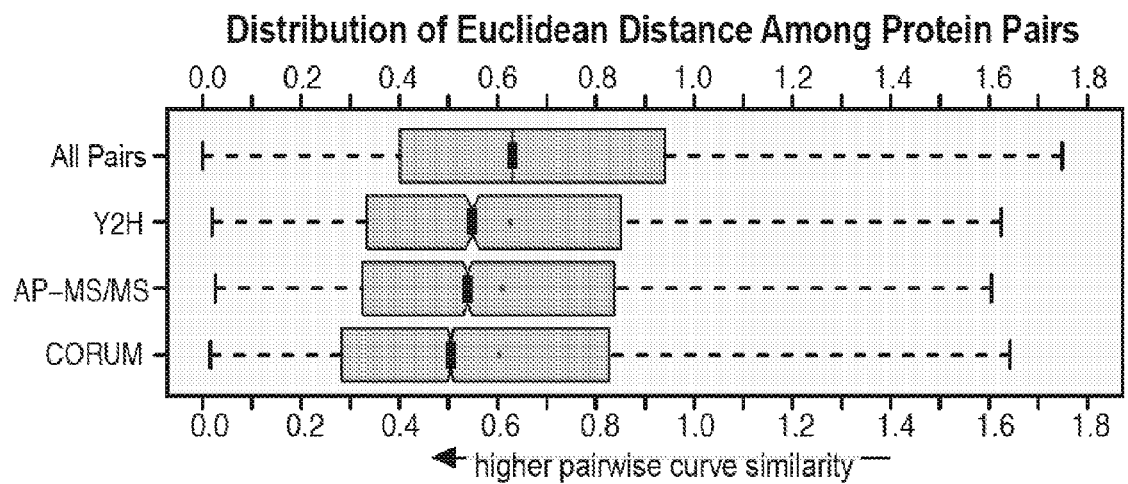
Figure 25:
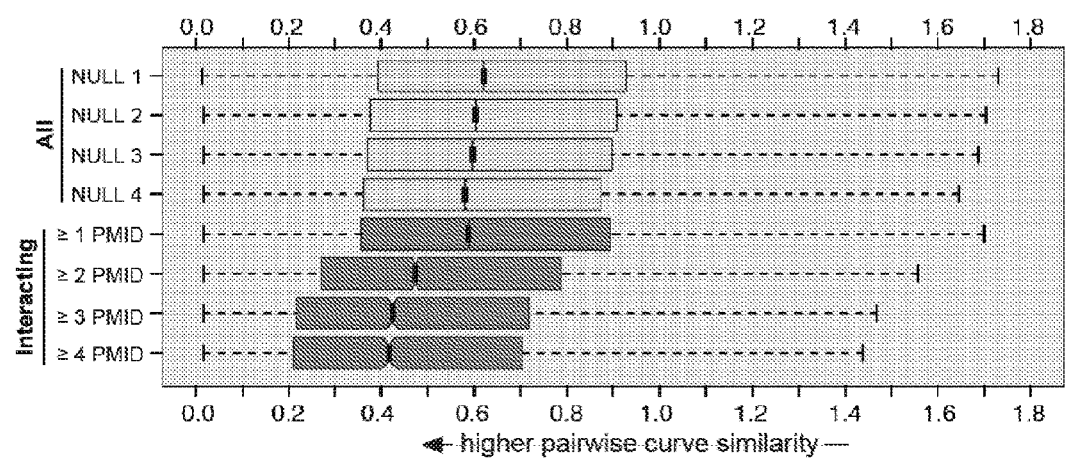
FIG. 25 shows a horizontal box plot that represents the null distributions of curve similarity among proteins in each filtered set of interaction data. NULL1, NULL2, NULL3 and NULL4 are curve similarity distribution generated from all protein in interaction data reported by PMID≥1, PMID≥2, PMID≥3 and PMID≥4 respectively.

To evaluate the generality of PCA, melting curves for 7693 human proteins were collated from eight MS-CETSA experiments of the same K562 lysate (FIG. 3). 111,776 protein-protein interactions were assembled and annotated in BioGRID, InAct, and MINT databases occurring among the 7693 proteins. Using Euclidean distance as an inverse measure of curve similarity, it was observed that interacting protein pairs generally have higher curve similarity than all protein pairs ($P<2.2\times10^{-16}$, one-tailed Mann-Whitney test, FIG. 4A). This similarity is more pronounced for interactions reported by multiple publications (FIG. 4A and FIG. 25). High curve similarity was also observed for interactions from two recent large-scale studies using yeast two-hybrid (Y2H) and affinity purification (AP)—MS/MS, and for subunit pairs of complexes in the CORUM database (FIG. 4B). Thus, it is unlikely that the observed PCA signatures arose from ascertainment bias and the experimental methods used.

Figure 5:
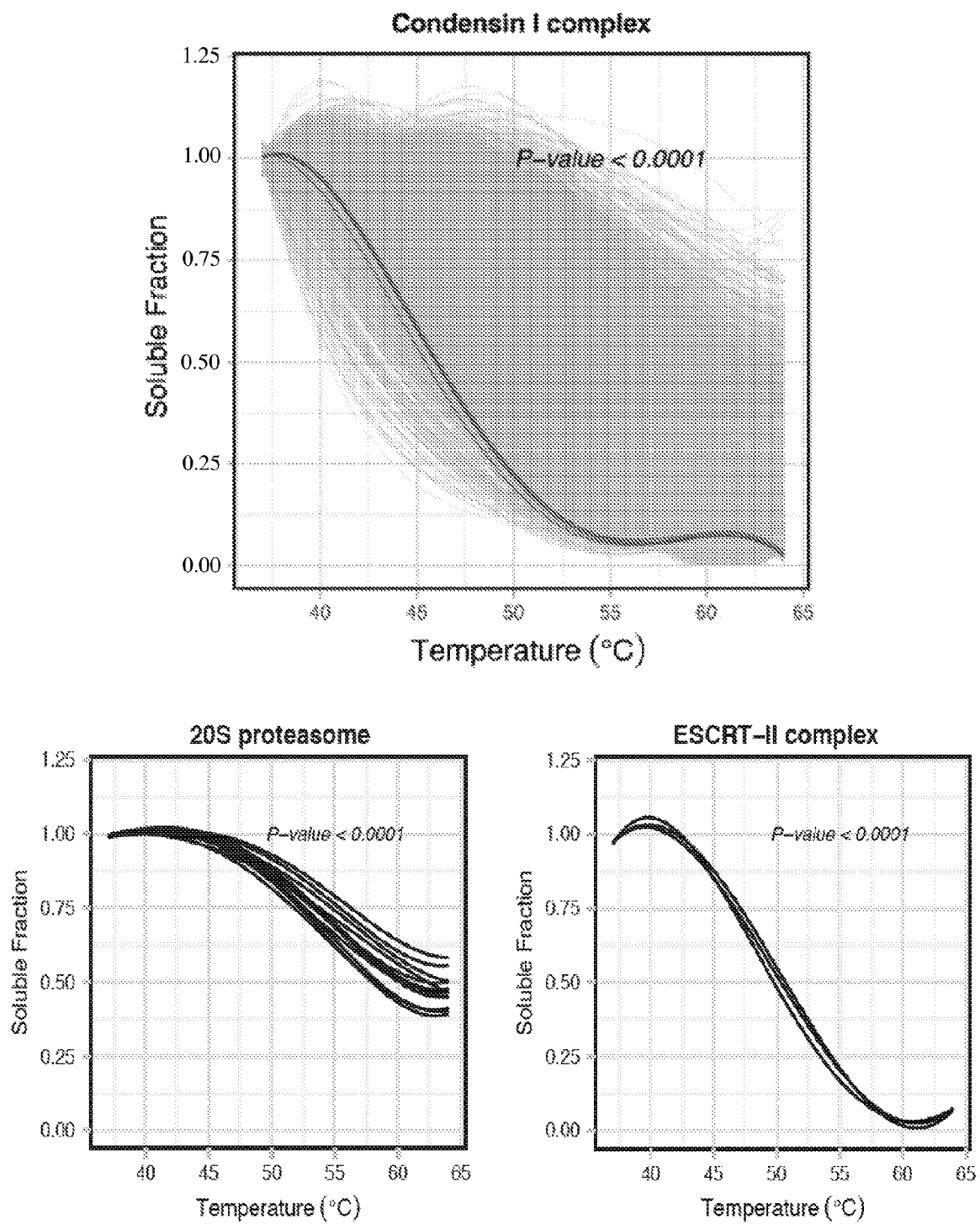
FIG. 5 shows 9 sigmoid graphs that represent melting curves of selected protein complexes: condensin complex (melting curves of ~4000 other proteins are plotted in grey), 20S proteasome, ESCRT-II complex, Arp2/3 protein complex, BAF complex, anaphase-promoting complex, BLOC-1 (biogenesis of lysosome-related organelles complex 1), conserved oligomeric Golgi (COG) complex and multisynthetase complex. Black lines represent complex subunits.
Figure 5:
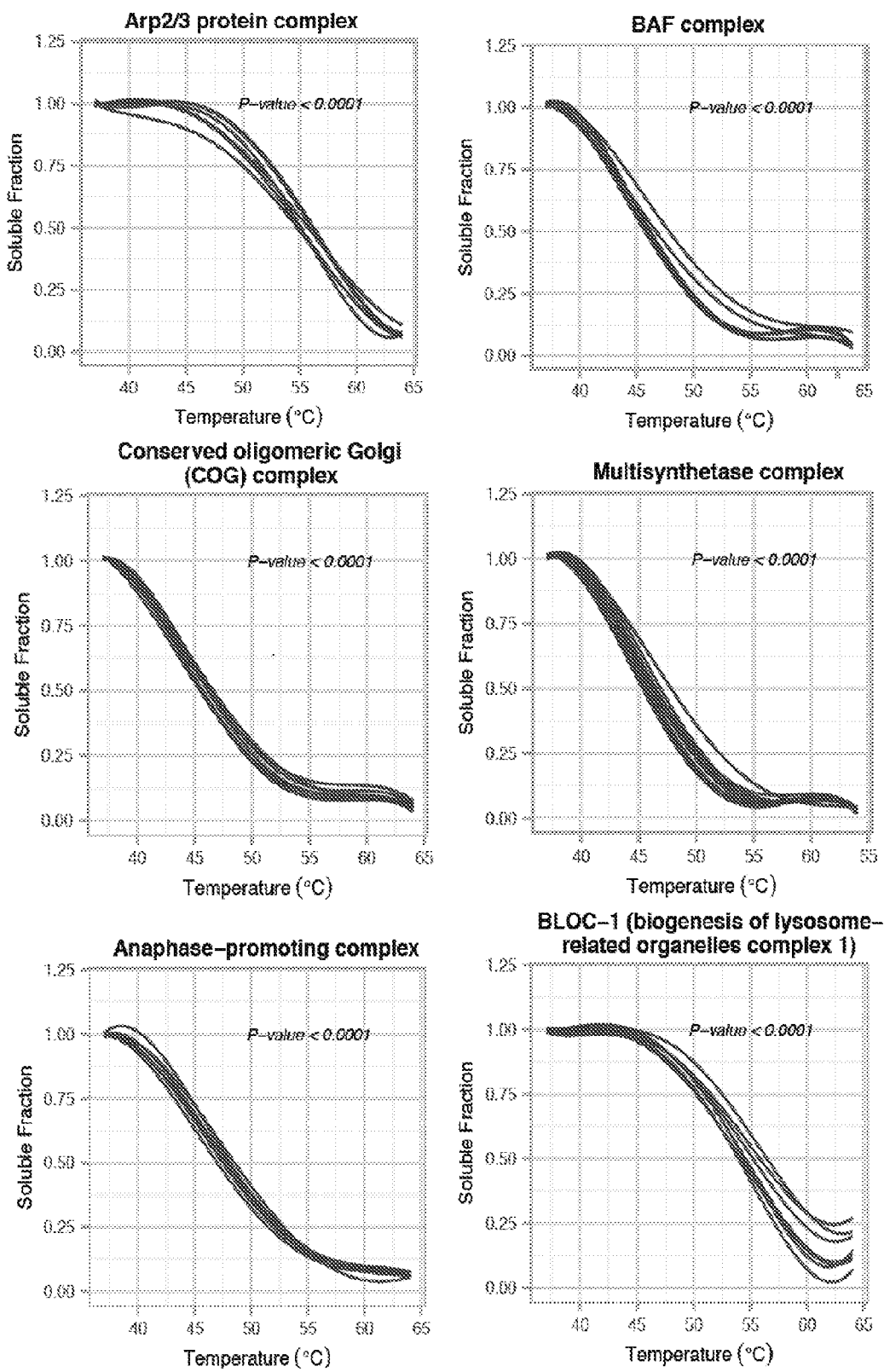

The average curve similarity was computed among all subunit pairs of each protein complex and assessed PCA signatures at the protein complex level. For the 558 nonredundant human complexes having at least three subunits with melting curves, 160 exhibited nonrandom PCA signatures among subunits collectively (P<0.05, FIG. 5).

Example 2

PCA Signature is Stronger in Data from Intact Cells

Figure 6:
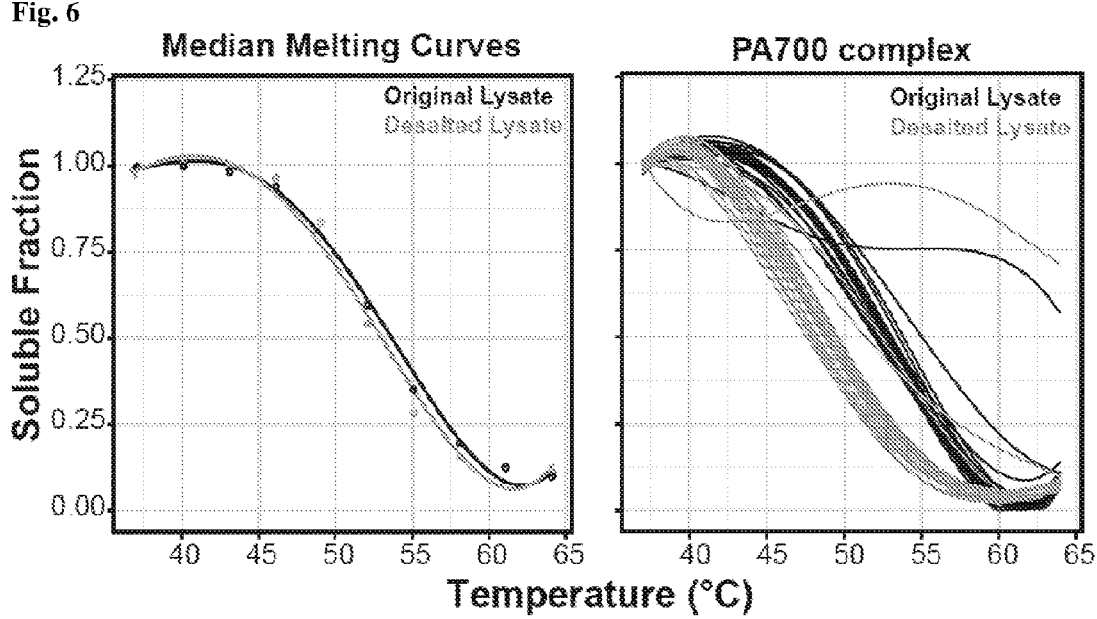
FIG. 6 shows 2 sigmoid graphs that represent the median (left) of melting curves for all quantified protein and the medians of melting curves (right) for subunits of PA700 complex, wherein the cell lysates has undergone desalting.
Figure 26:
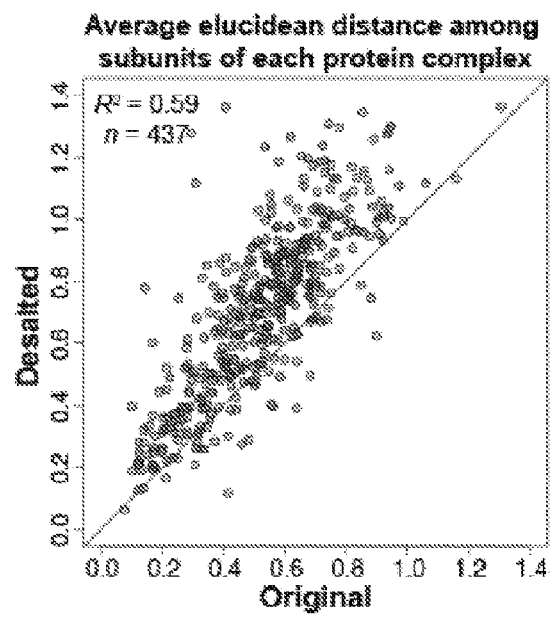
FIG. 26 shows 3 scatter plots that represent the average Euclidean distance among subunits of each protein complex on different samples. (A) shows the effect of desalting cell lysate on average melting curve similarity of protein complexes. CETSA experiments were performed on the original and desalted samples. Only proteins found in both datasets were used in the computation. (B) shows the reproducibility of average Euclidean distance computed for each protein complex across two lysate CETSA experiments from two different batches of K562 cells. (C) shows the reproducibility of average Euclidean distance computed for each protein complex across two lysate CETSA experiments from two different batches of K562 cells, but only proteins with at least three peptides with quantification information are considered and need not be unique.
Figure 26:
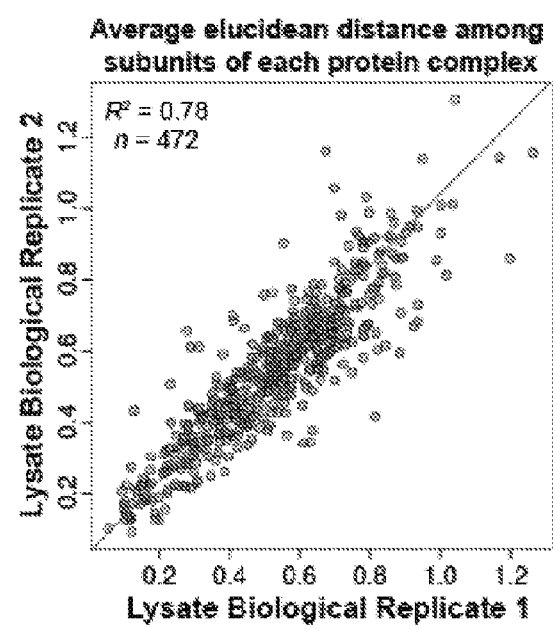
Figure 26:
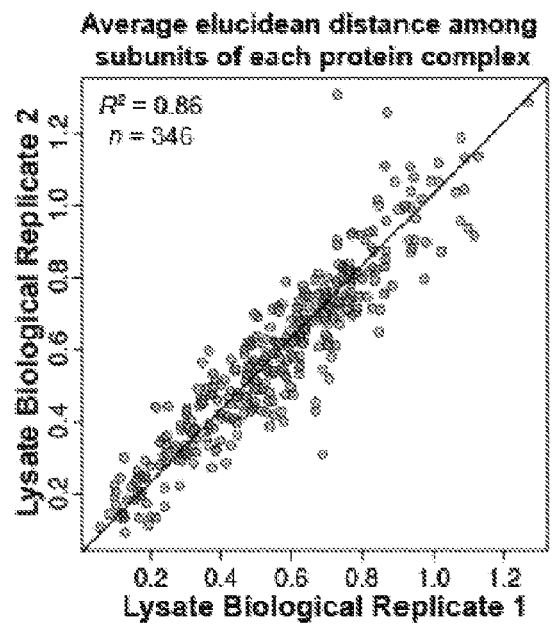
Figure 27:
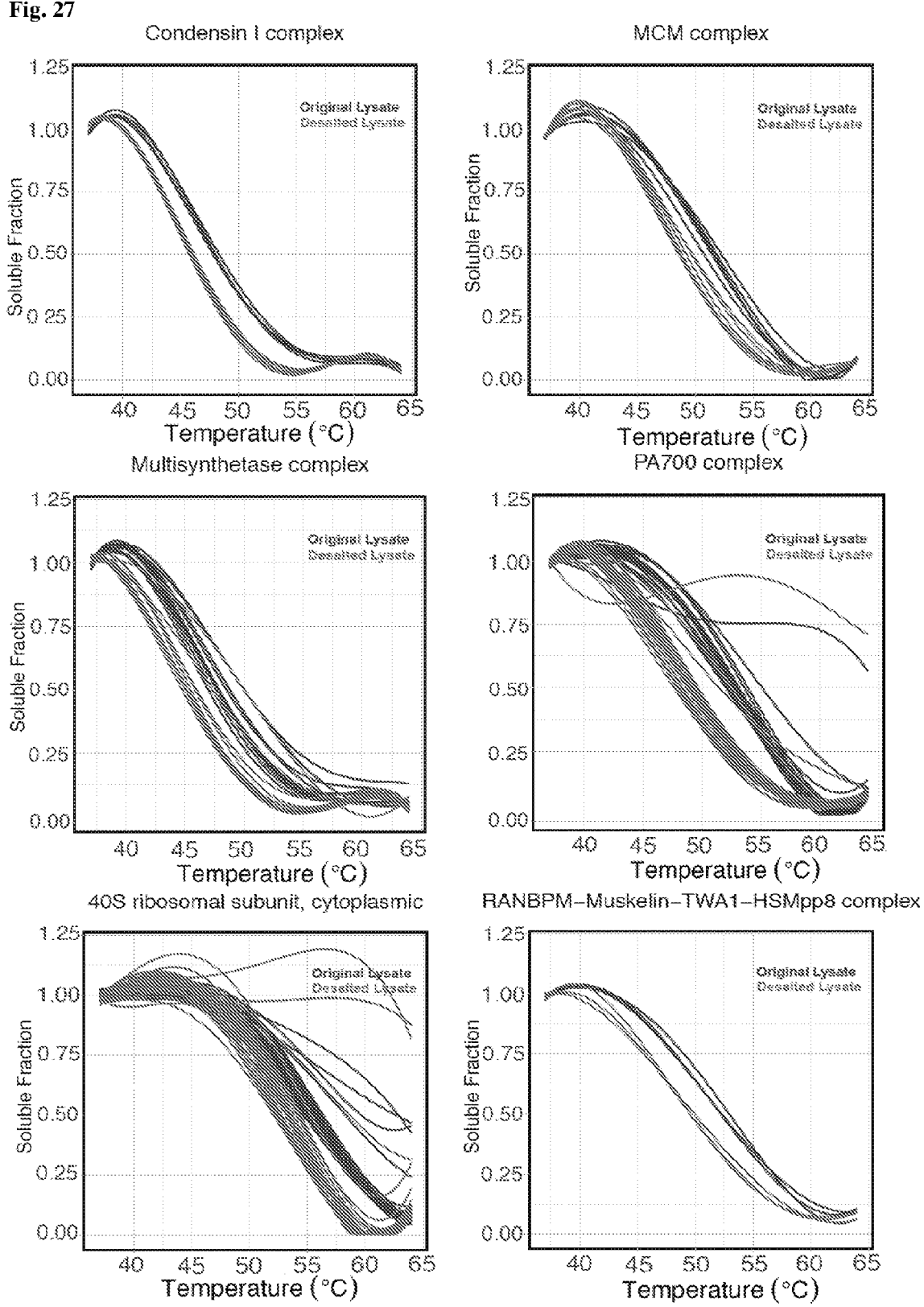
FIG. 27 shows 6 sigmoid graphs that represent the melting curves of visually identified subset of protein complexes that have non-random similarity in melting curves among its subunits but seems thermal destabilized from desalting as a whole complex. The identified subset of protein complexes are condensin I complex, MCM complex, multisynthetase complex, PA700 complex, 40S ribosomal subunit (cytoplasmic) and RANBPM-Muskelin-TWA1-HSMpp8 complex.
Figure 28:
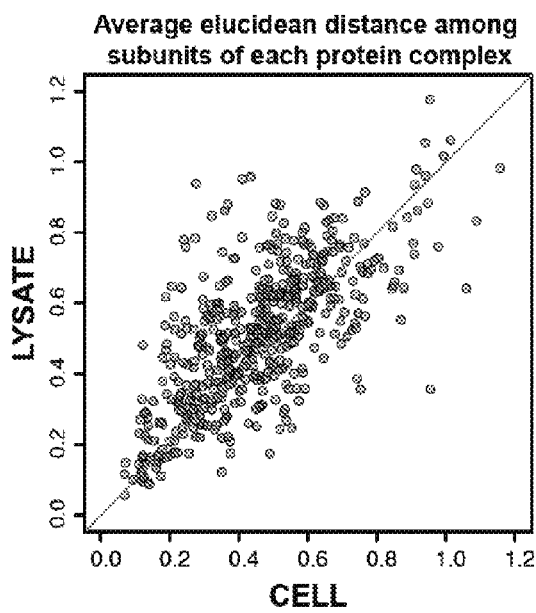
FIG. 28 shows 2 scatter plots and 2 box plots that represents average Euclidean distance for comparison of intact cell and lysate CETSA data in term of protein complexes. (A) shows a scatterplot of average Euclidean distance among subunits computed for each protein complex. (B) shows a boxplot for distribution of average Euclidean distance among subunits computed for each protein complex. (C) shows a scatterplot of average Euclidean distance among subunits computed for subset of protein complexes that have non-random PCA signature in either intact cell or lysate CETSA data. (D) shows a boxplot of average Euclidean distance among subunits computed for subset of protein complexes that have non-random PCA signature in either intact cell or lysate CETSA data.
Figure 28:
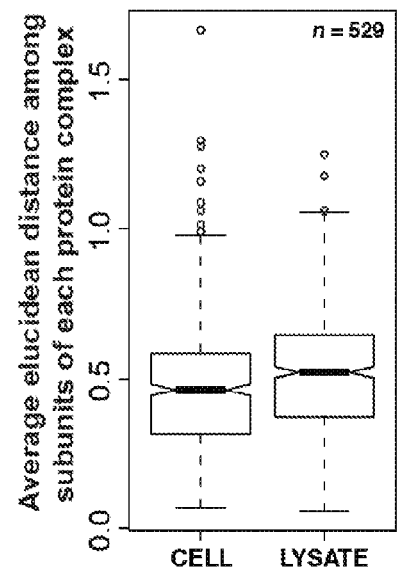
Figure 28:
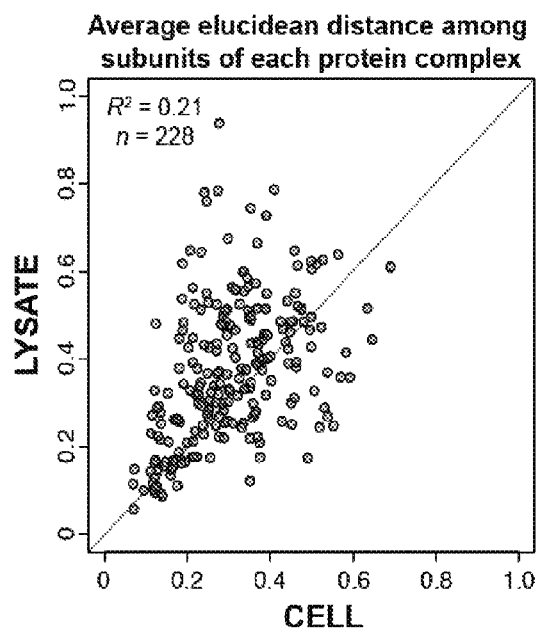
Figure 28:
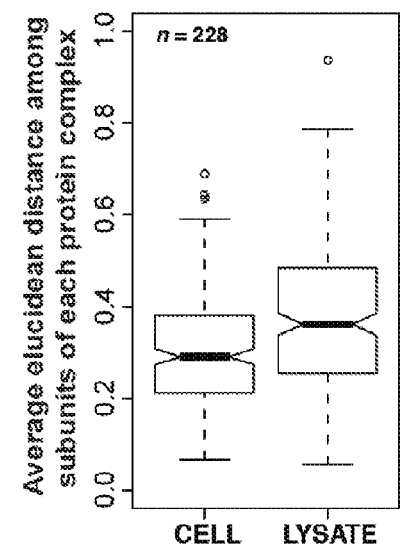

Next, MS-CETSA data was obtained from the K562 cell lysate that was depleted of low-molecular weight (LMW) ligands by desalting. Decreased average curve similarity was observed for most protein complexes (~88%, FIG. 26A), suggesting that LMW ligand depletion caused increased complex dissociation. However, multiple protein complexes with negligible changes in PCA but with melting curves of all subunits shifted similarly were observed, such as the PA700 proteasome subcomplex that could be due to adenosine 5'-triphosphate (ATP) depletion (FIG. 6 and FIG. 27). Thus, whole-protein complexes can remain intact yet thermally destabilized by LMW ligand depletion. In comparison, MS-CETSA data from a new batch of K562 lysate shared good reproducibility with the previous lysate (Pearson's R=0.88). Higher reproducibility was observed (FIG. 26C) for proteins with at least three quantified peptides in each data set, and thus combined existing and new data sets for subsequent analysis.

Figure 7:
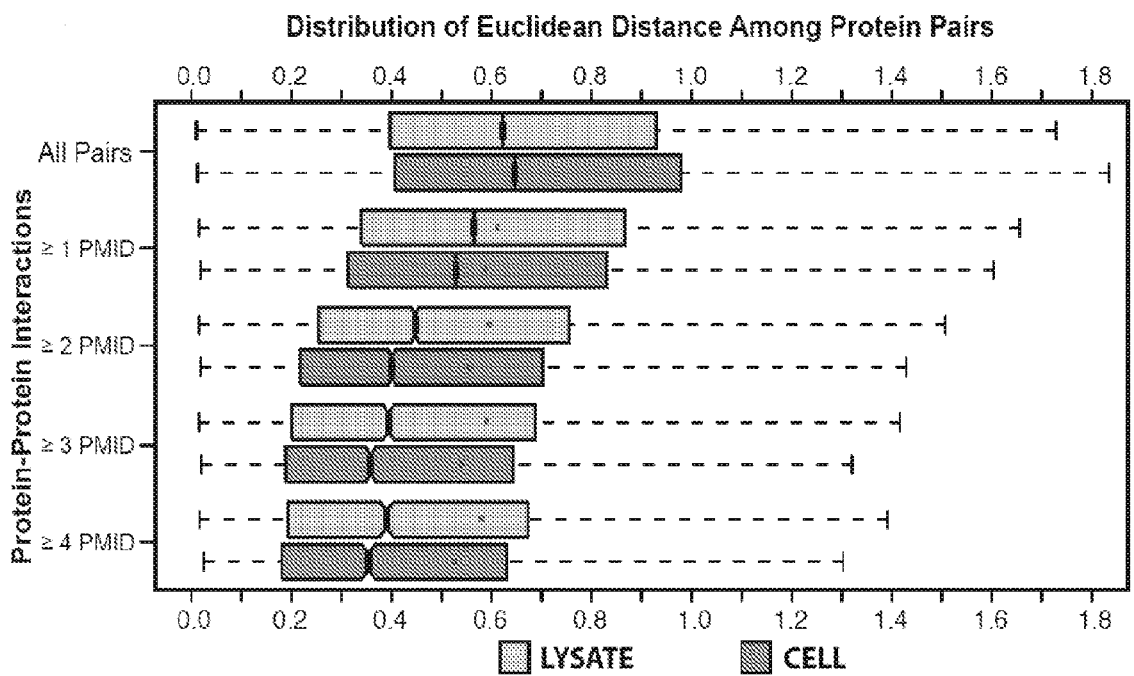
FIG. 7 shows a horizontal box plot that represents the distribution of melting curve similarities (based on Euclidean distance among protein pairs) of known interacting protein pairs computed from cell lysate and intact cell data. Dark grey dots indicate the median of all protein pairs of each respective protein subset.
Figure 8:
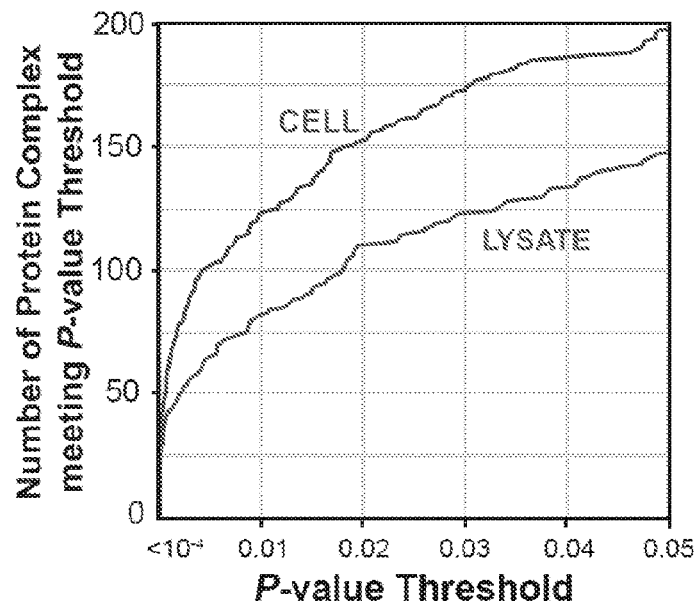
FIG. 8 shows a scatter plot that represents the number of CORUM protein complexes with non-random PCA behaviour at different statistical threshold computed from proteins derived from cell lysate and intact cell.
Figure 29:
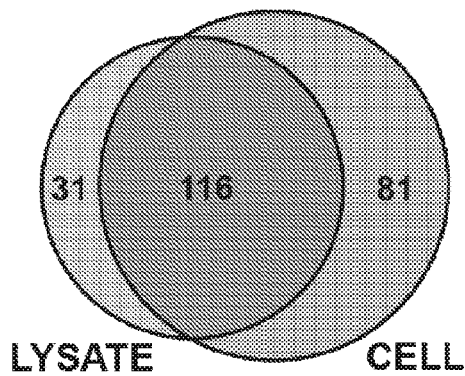
FIG. 29 shows a Venn diagram that represents protein complexes with non-random PCA signature in intact cell and lysate CETSA data.
Figure 30:
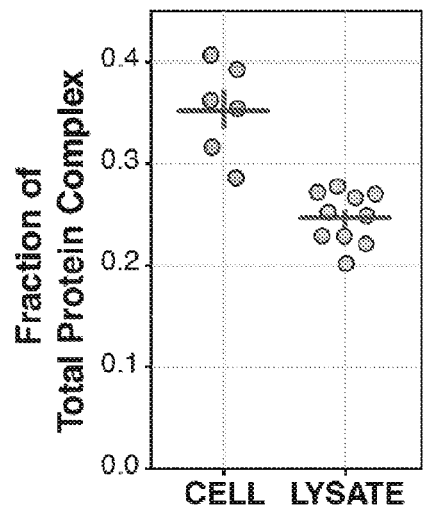
FIG. 30 shows a scatter plot that represents the fraction of total protein complex in cell and in lysate. Portion of qualified protein complexes that have non-random PCA behaviour in individual lysate and cell datasets. Statistical threshold is set at P-value<0.05. Each node represents a dataset; red horizontal bar denotes average value within each data type with vertical bar representing standard error of mean.

Six MS-CETSA experiments were performed on intact K562 cells. Melting curves of all protein pairs were observed to be statistically more similar in the lysate data (FIG. 7), whereas those for interacting protein pairs are statistically more similar in intact cell data (FIG. 7). Protein complexes were also observed to have better average curve similarity among subunits in intact cell data than in lysate data (FIGS. 28A to D). Overall, intact cell data reveal more protein complexes with nonrandom PCA signatures than the lysate data (FIG. 8, FIG. 29 and FIG. 30).

Figure 9:
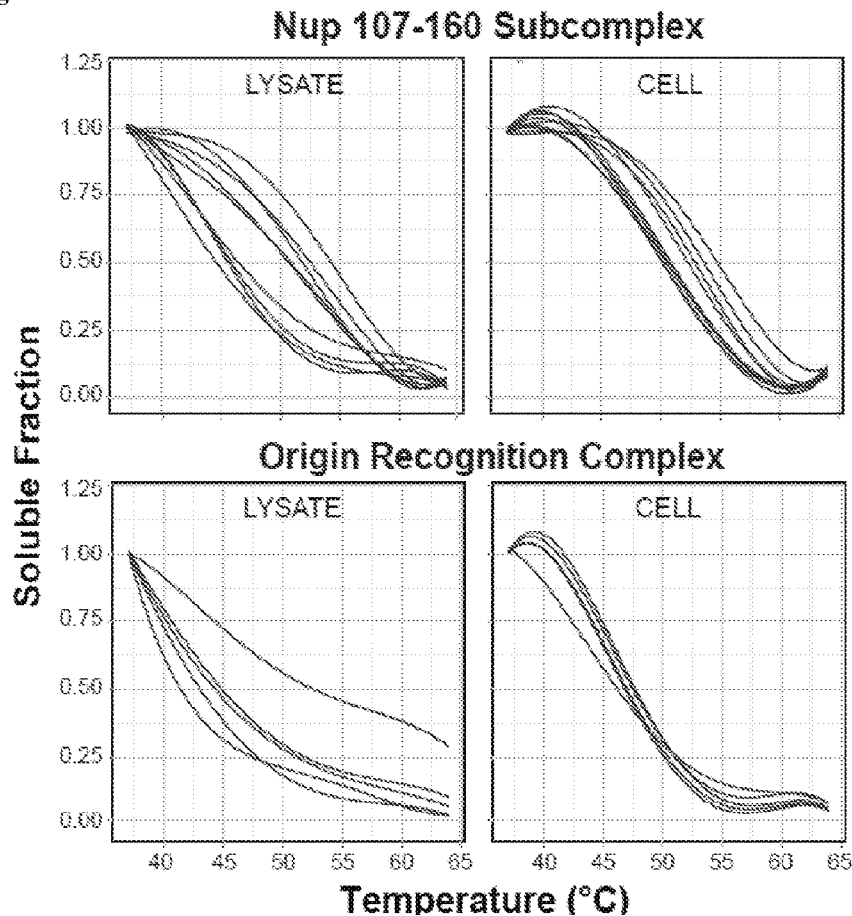
FIG. 9 shows 4 sigmoid graphs that represent the melting curves for subunits of DNA-chromatin- and membrane-associated complexes Nup 107-160 subcomplex and origin recognition complex in cell lysate and intact cell.
Figure 31:
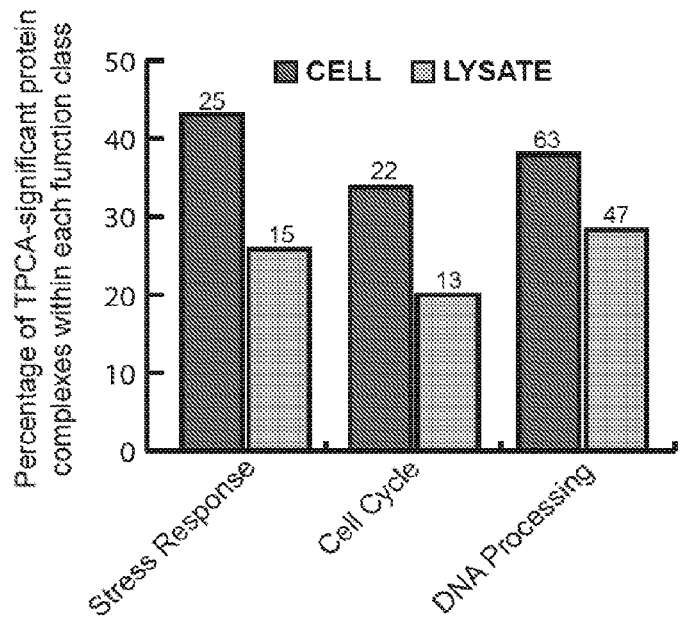
FIG. 31 shows a column chart of the percentage of PCA-significant protein complexes with each functional class in cell and in lysate under different categories, stress response, cell cycle and DNA processing. The number of protein complexes under the three CORUM's function categories that had been identified to be statistically enriched in PCA-significant protein complexes either intact cell or lysate data.

PCA-significant protein complexes in stress response, cell cycle, and DNA processing pathways are statistically enriched in intact cell data over lysate data (FIG. 31). Many DNA-chromatin-associated complexes and membrane-associated complexes—as exemplified by the Nup 107-160 nuclear pore subcomplex and the origin recognition complex, respectively (FIG. 9)—exhibit significant PCA signatures only in intact cells, presumably due to disruption of DNA-chromatin and native membranes in cell lysate. Analysis suggests that the replication factor complex C (RFC) remains assembled in both intact cell and lysate (FIG. 10A, top) but that the whole complex is thermally destabilized in lysate (FIG. 10A, top left), presumably due to the absence of DNA-chromatin.

Figure 10:
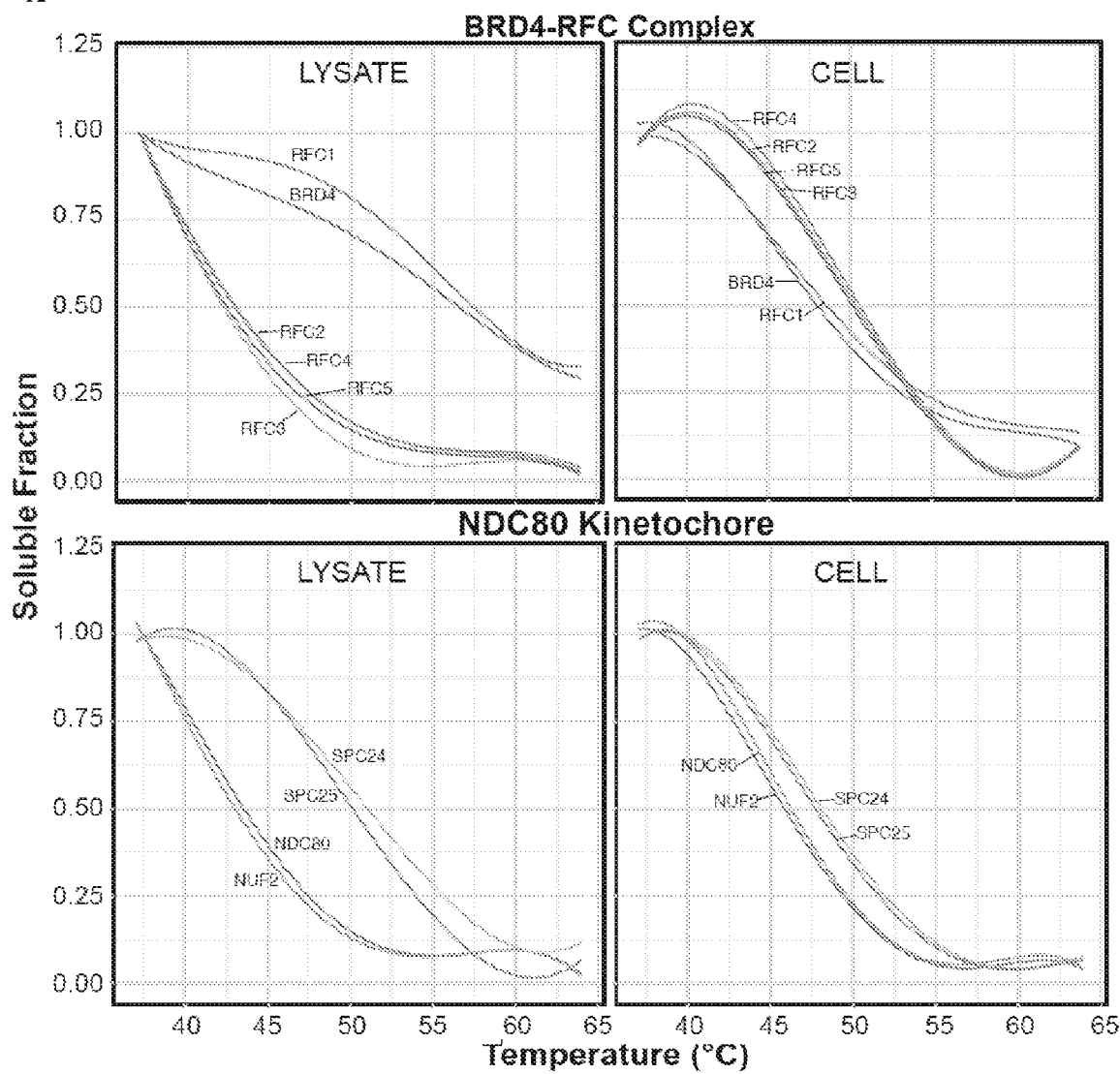
FIG. 10 shows 6 sigmoid graphs that represent the melting curves of the examples of subcomplexes that differ in cell and in lysate, such as (A) the BRD4-RFC complex, NDC80 Kinetochore, and (B) 40S Ribosomal subunit and 60S ribosomal subunit in cell lysate and intact cell.
Figure 10:
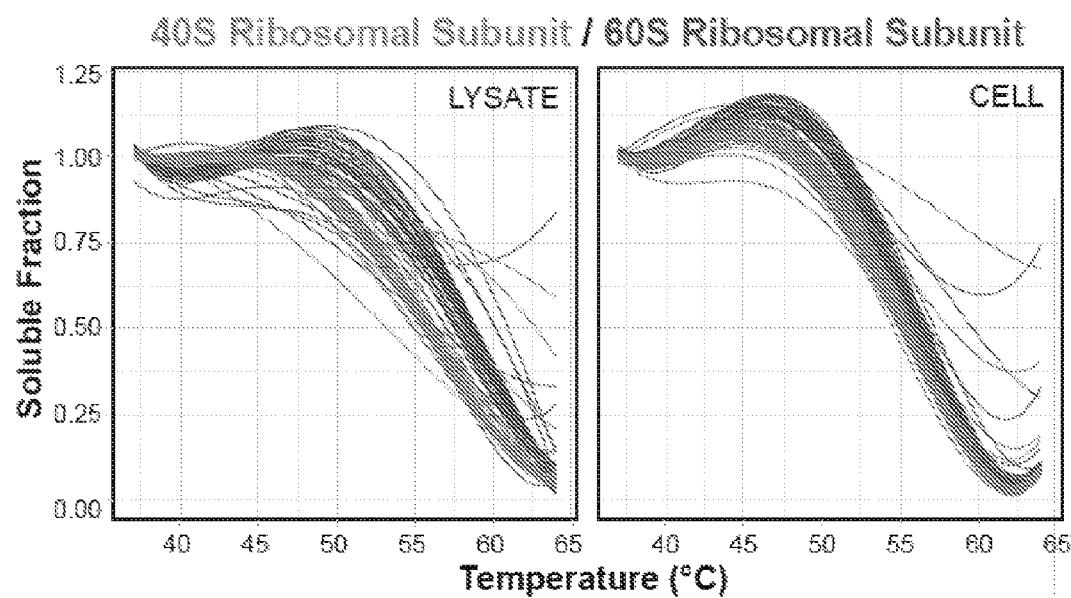
Figure 11:
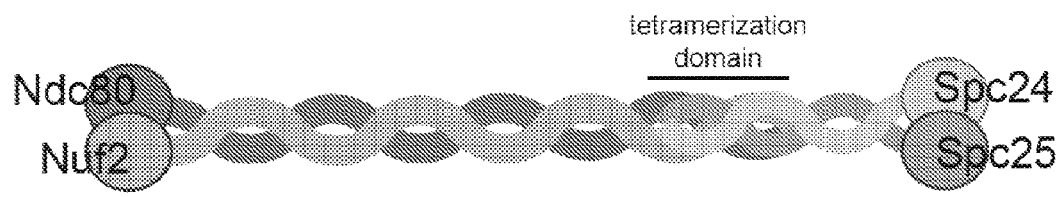
FIG. 11 shows a schematic of the structure for NDC80 Kinetochore.

Many instances were observed in which subcomplexes exhibit distinct PCA signatures between intact cell and lysate data sets. For example, the 40S and 60S ribosomal subcomplexes each have subunits with similar curves that shifted closer to the other subcomplex in intact cell data (FIG. 10B), presumably because more fully assembled ribosomes are translating mRNA in cells than in lysate. Another example is the NDC80 kinetochore complex with two distinct subunit groups based on melting curves that are more similar to each other in intact cell data than in lysate data (FIG. 10A, bottom). The two distinct subunit groups correspond to the two stable heterodimers that are associated with each other through a short tetramerization protein region (FIG. 11). PCA analysis suggests that the two subcomplexes had dissociated in lysate. These observations suggest that PCA can reveal fundamental differences in protein complex organization and their functional states.

Example 3

Figure 12:
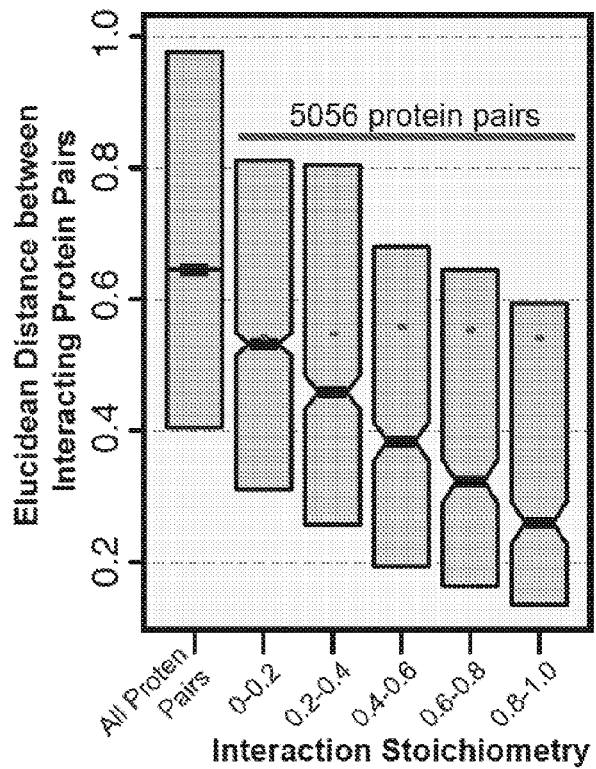
FIG. 12 shows 4 box plots that represents data of the correlation of PCA signature (intact cell MS-CETSA data) with (A) protein interaction stoichiometry, (B) protein abundance stoichiometry of known interacting protein pairs. (C) shows protein pairs with high stoichiometry in both parameters. (D) shows the multiplication of interaction and abundance stoichiometry correlates better with PCA signature exhibiting the highest PCA signature.
Figure 12:
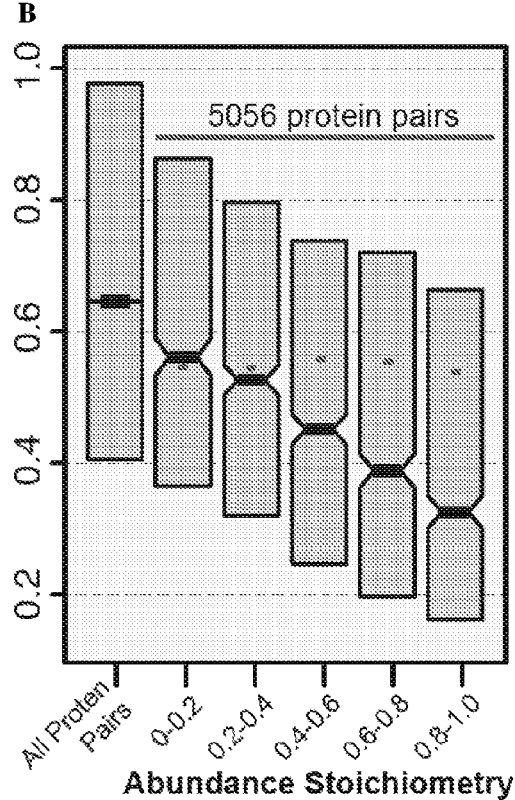
Figure 12:
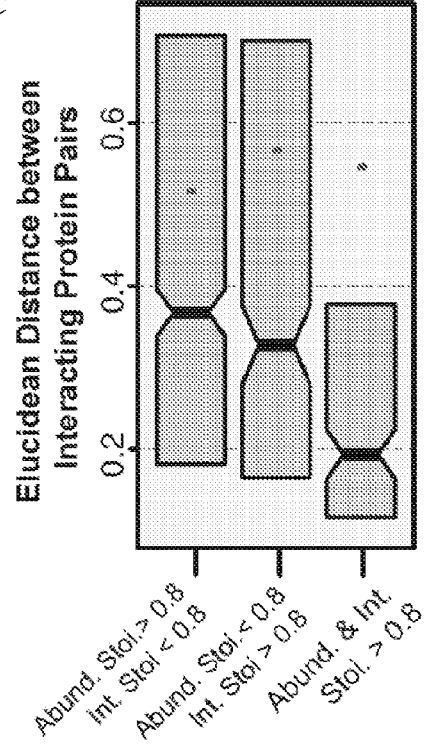
Figure 12:
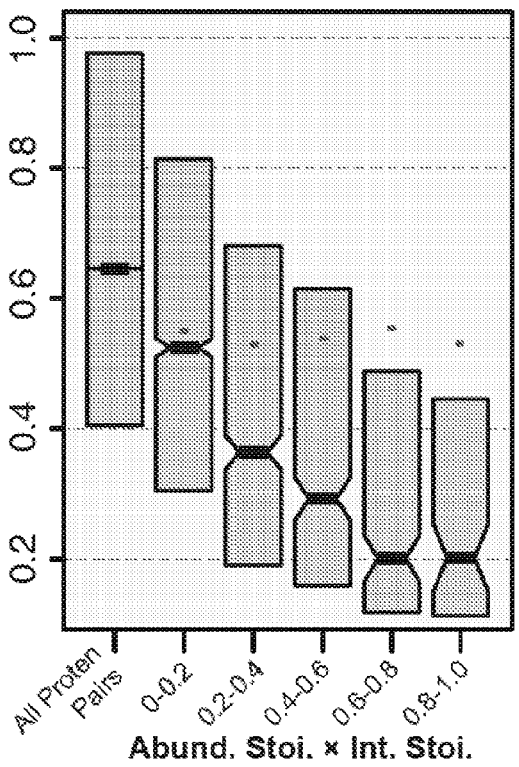
Figure 32:
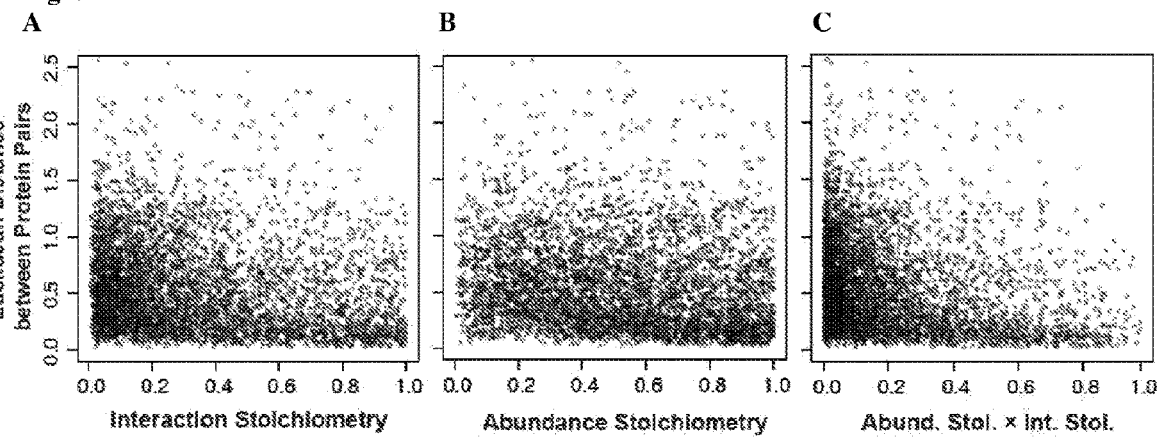
FIG. 32 shows 3 scatter plots of Euclidean distance versus different parameters. (A) shows Euclidean distance versus interaction stoichiometry. (B) shows Euclidean distance versus abundance stoichiometry. (C) shows Euclidean distance versus their multiplied values for interacting protein pairs.
Figure 33:
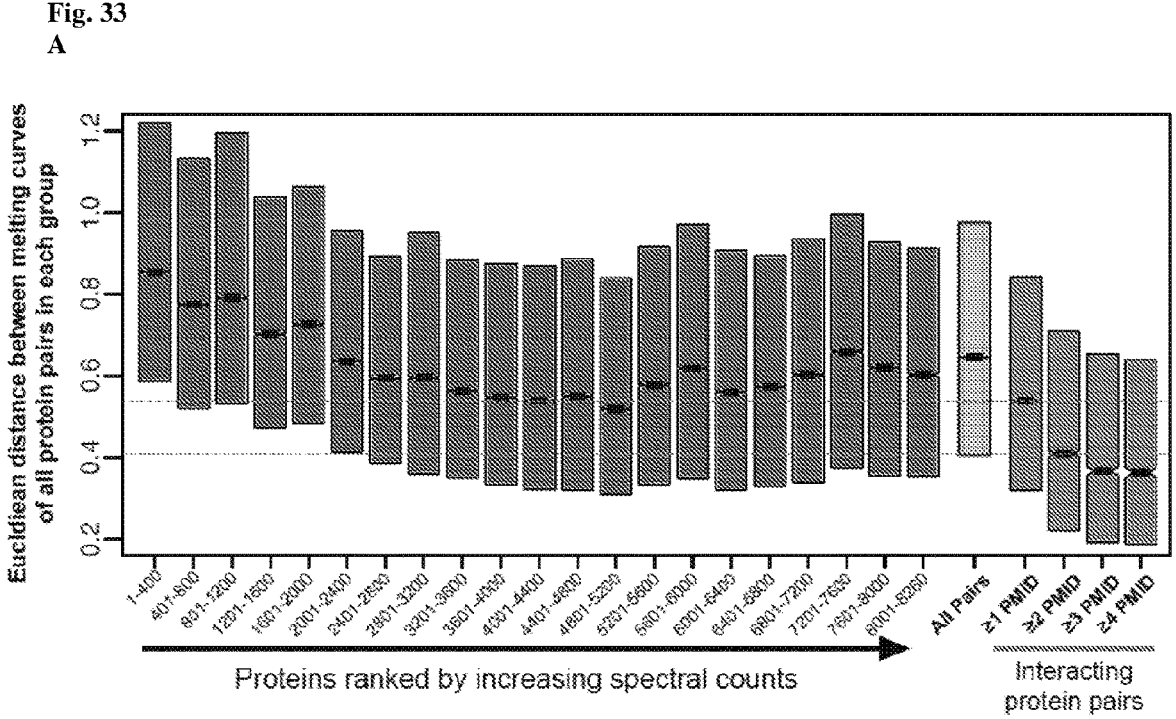
FIG. 33 shows 3 box plots that represent the Euclidean distance between melting curves of all protein pairs in each group, wherein protein pairs with similar abundance do not exhibit strong PCA signature. (A) represents that proteins are first sorted by spectral count and divided into groups of 400 proteins each. Euclidean distance between melting curves (intact K562 data) of every possible pairwise combination of proteins in each group is computed, and distribution visualized with boxplots. (B) represents the similar analysis for proteins will most reproducible curves (defined as those with quantifying PSM>10). (C) represents similar analysis to (A) and (B), but using absolute protein abundance estimated with the proteomic ruler approach.
Figure 33:
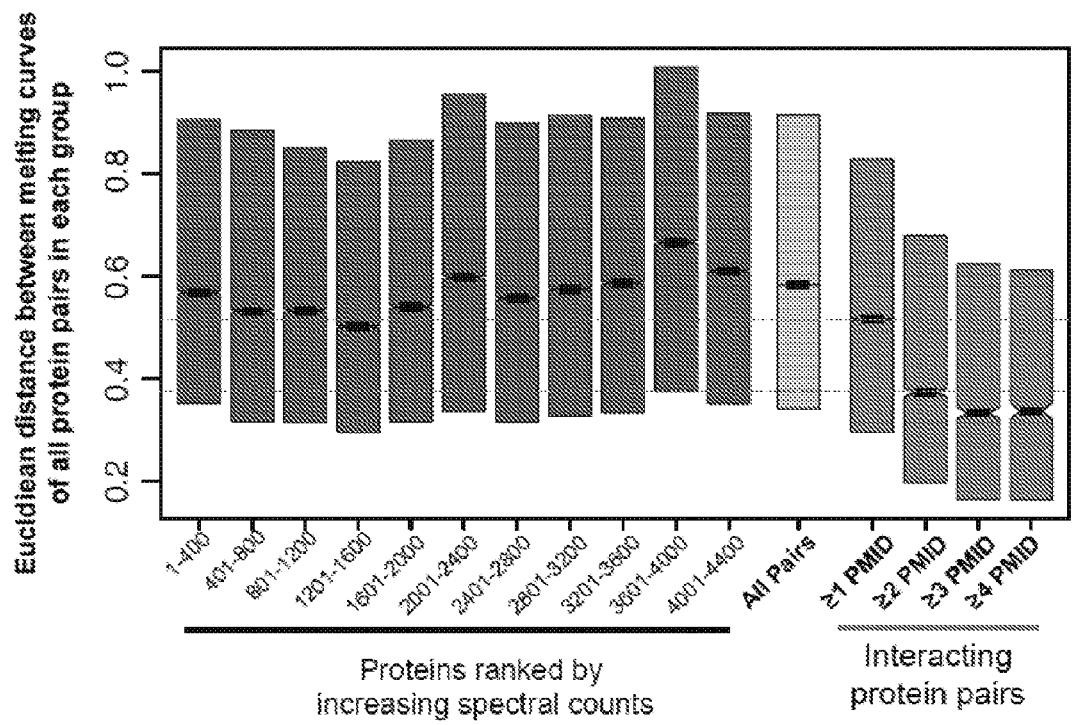
Figure 33:
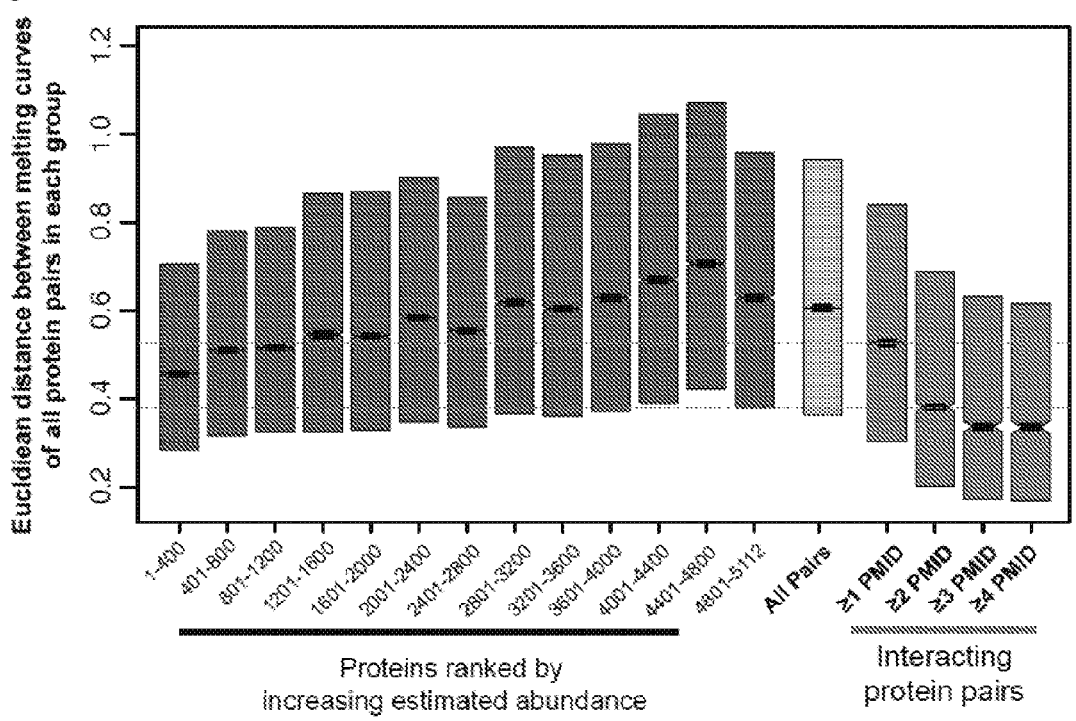

PCA Signature Interaction Stoichiometry and Abundance Stoichiometry Between Interacting Proteins The stoichiometry of interaction and abundance between subunits in a complex can potentially influence its PCA signature. Such data was analysed for the interacting protein pairs reported with highest confidence and observed positive correlation of the PCA signature with interaction stoichiometry (Spearman's R=−0.22, P<0.001, FIG. 12A and FIG. 32A) and abundance stoichiometry (Spearman's R=−0.21, P<0.001, FIG. 12B and FIG. 32B). The protein pairs with both interaction stoichiometry and abundance stoichiometry greater than 80% exhibit much stronger PCA signatures than those meeting the two criteria separately (FIG. 12C). In comparison, proteins paired solely by similar abundance do not exhibit strong PCA signatures (FIG. 33A to C). Accordingly, multiplying interaction stoichiometry with abundance stoichiometry results in values that correlate better with PCA signature (Spearman's R=−0.27, P<0.001, FIG. 12D and FIG. 32C). Thus, interaction and abundance stoichiometry between interacting proteins are intrinsically captured by PCA, albeit semiquantitatively.

Figure 13:
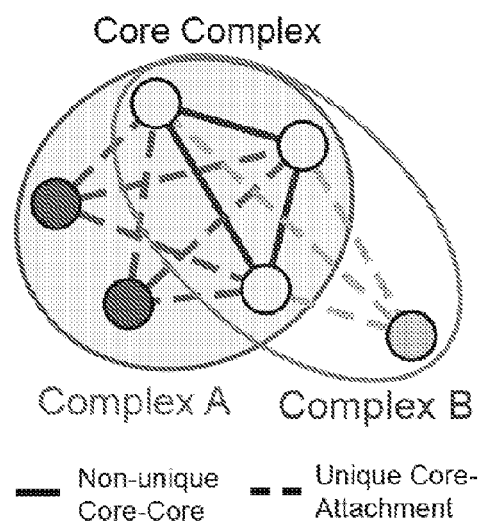
FIG. 13 shows a schematic that represents the core attachment model for functional organization of protein complexes.
Figure 14:
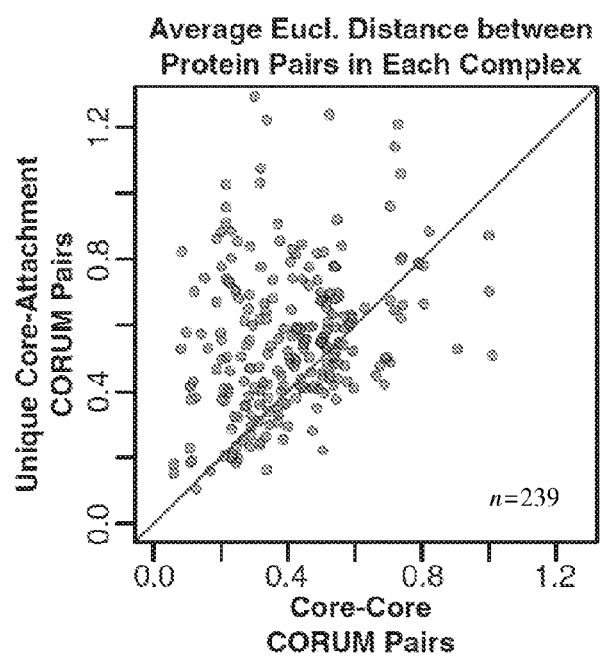
FIG. 14 shows a dot plot that represents data showing core-attachment protein pairs of a complex generally exhibit weaker PCA signature than core-core protein pairs. Each dot represents a protein complex.

Under the core-attachment model, subsets of proteins form the stable core of protein complexes that are differentially or temporally bound by other proteins. This model was investigated with PCA, comparing melting curves of protein pairs from the complex core to curves for pairs between the core and the attachment subunits (FIG. 13). The core-core pairs were identified in each complex as those found in two or more other CORUM complexes and core-attachment pairs as those found in that complex only. For most of the complexes, the PCA signature of core-core pairs is either similar to or much stronger than that of the core-attachment pairs (FIG. 14). This is in accordance with the core-attachment model in which core-attachment interactions generally occur at lower stoichiometry. Thus, PCA signature potentially encapsulates the temporal and core-attachment organization of many complexes.

Figure 34:
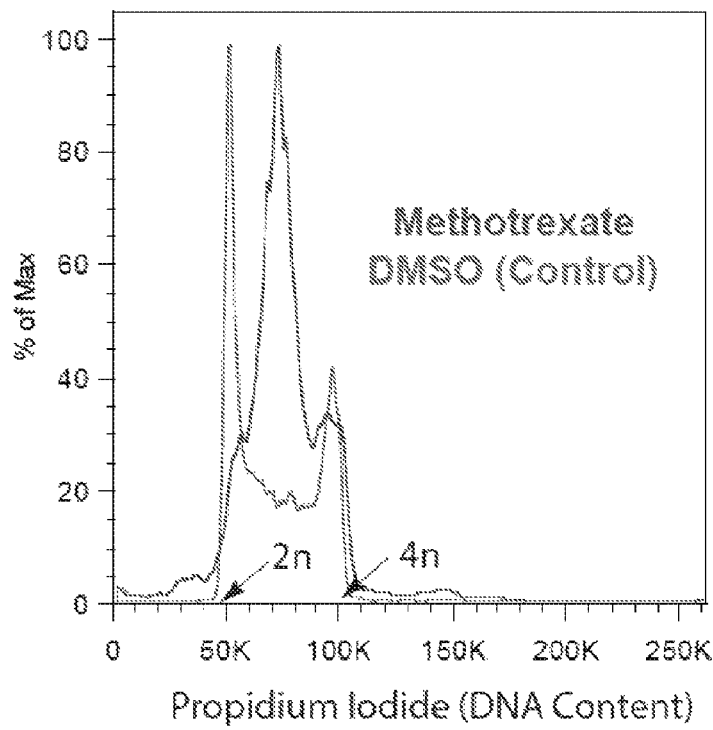
FIG. 34 shows a graph that represents DNA content analysis of methotrexate-treated and DMSO-treated K562 with FACS analysis of propidium iodide staining.

Next, PCA was explored for system-wide monitoring of protein complex dynamics between cell states. Intact cell MS-CETSA data was obtained from K562 cells arrested in the S phase of the cell cycle using methotrexate (FIG. 34) and from dimethyl sulfoxide (DMSO)-treated unsynchronized cells. Statistical significance was assessed for enhanced PCA (i.e., higher average curve similarity) observed for any CORUM complex (see materials and methods). 18 protein complexes, some containing overlapping subunits, were identified to have statistically enhanced PCA signature across both biological replicates in S phase-synchronized cells.

All but three identified modulated protein complexes had previously been implicated in the S phase. They include the CAF-1 complex (FIG. 15), which forms and localizes to the replication fork during S phase; the TREX-THO complex (FIG. 15) required for replication fork progression; and the TRAP complex required for S phase progression. Many chromatin-nucleosome remodeling and associated complexes were also identified, such as BAF (FIG. 15), LARC, and BRG1-SIN3A, consistent with the expected remodeling of chromatin during the S phase. Histone mRNAs were up-regulated prior to S phase but were rapidly degraded with halted DNA replication. Three modulated protein complexes—the mRNA decay complex, the exosome, and the integrator complex—were identified to be involved in histone mRNA degradation. Deletion of RRP6, a subunit of exosome, was reported to increase histone mRNA HTB1 during S phase, thus highlighting the role of this complex during S phase. Integrator complex was implicated in the processing of replication-dependent histone mRNAs.

Figure 15:
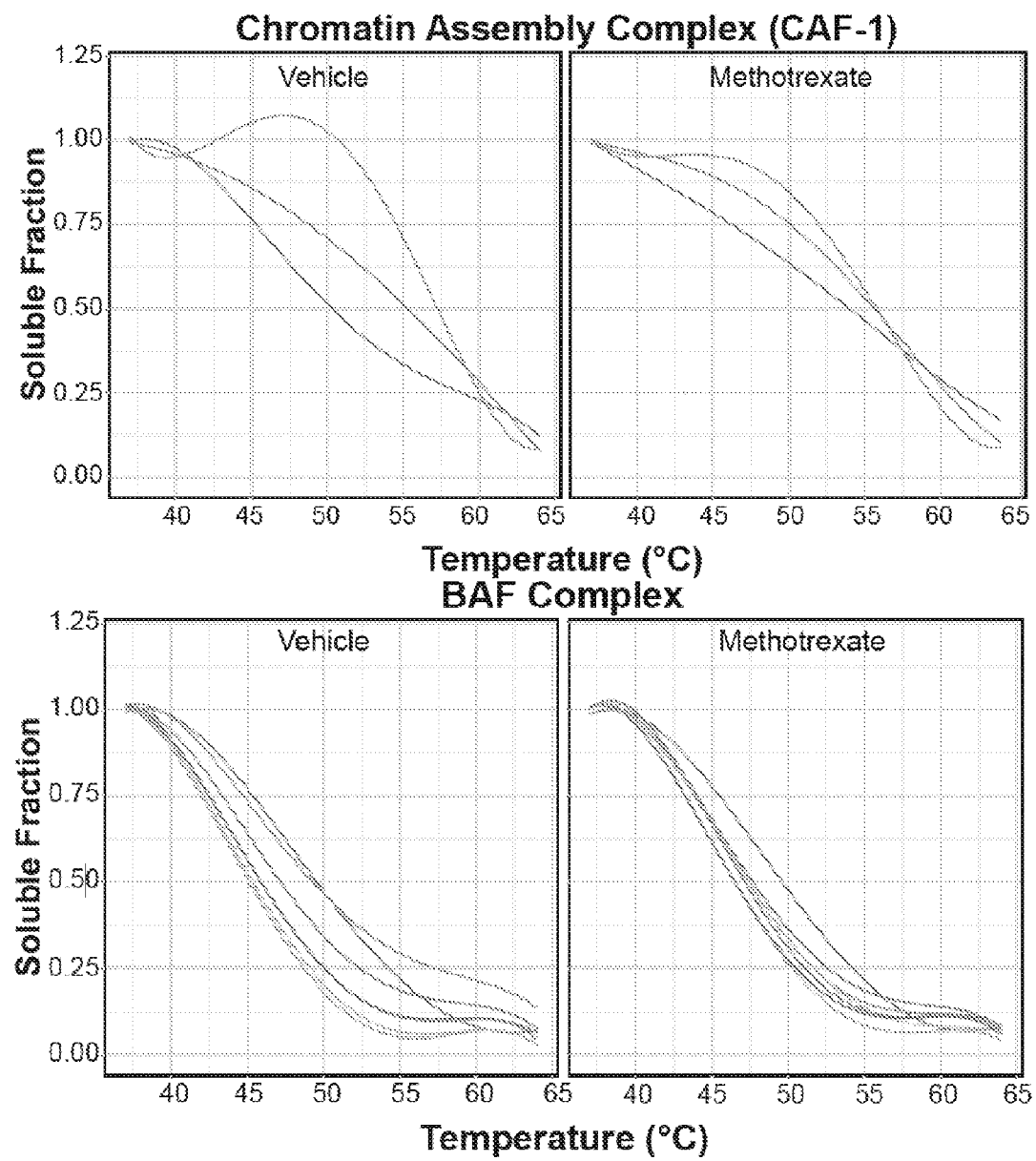
FIG. 15 shows 8 sigmoid graphs that represent the melting curves of subunits of the chromatin assembly complex (CAF-1), the chromatin-remodelling BAF complex, the TNFα/NFκB signalling complex and the TREX/THO complex from cells in different cellular conditions.
Figure 15:
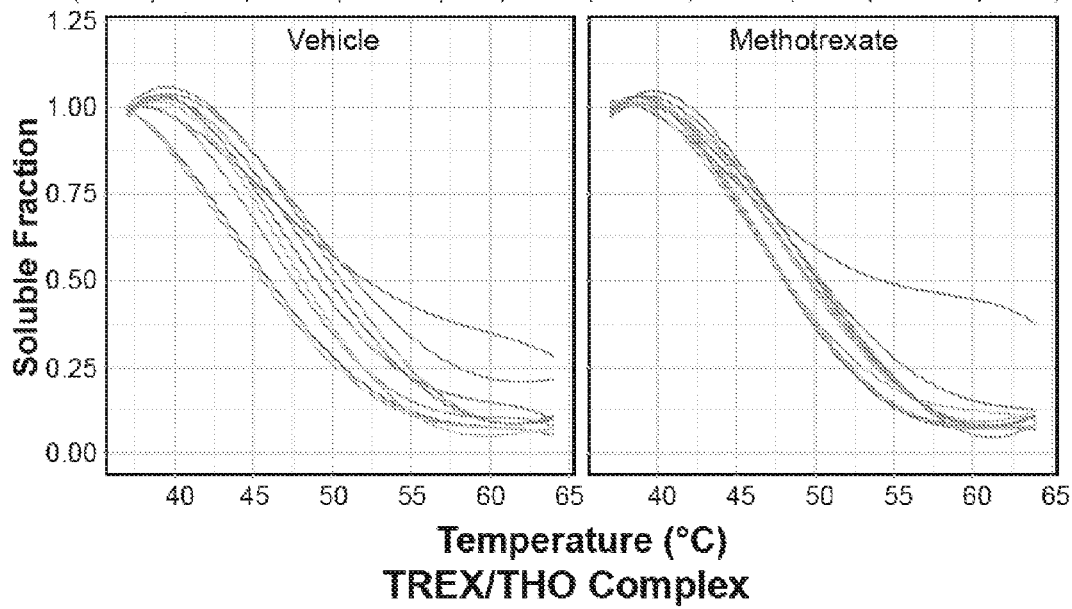
Figure 15:
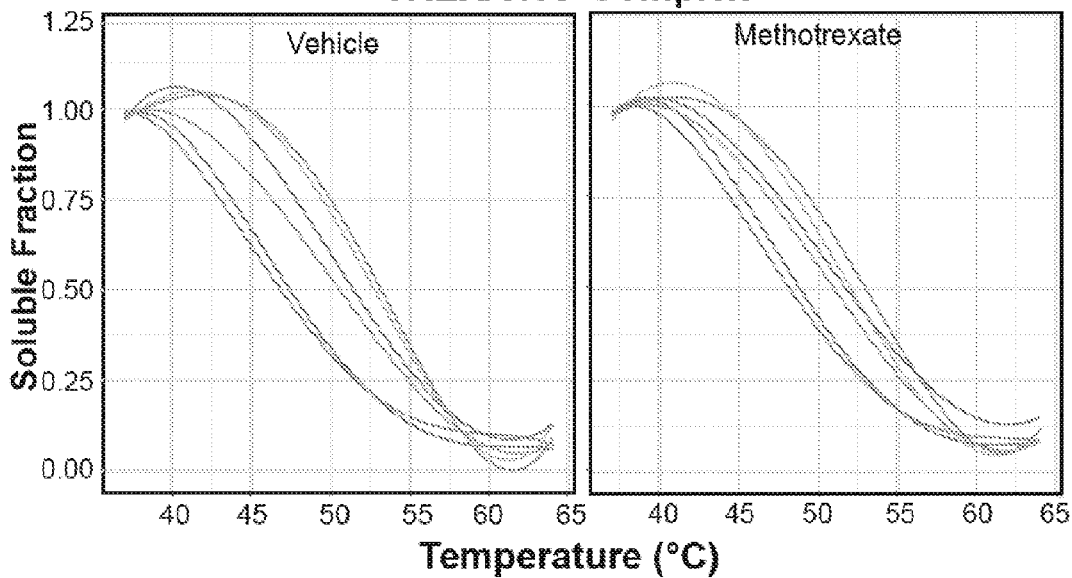
Figure 16A:
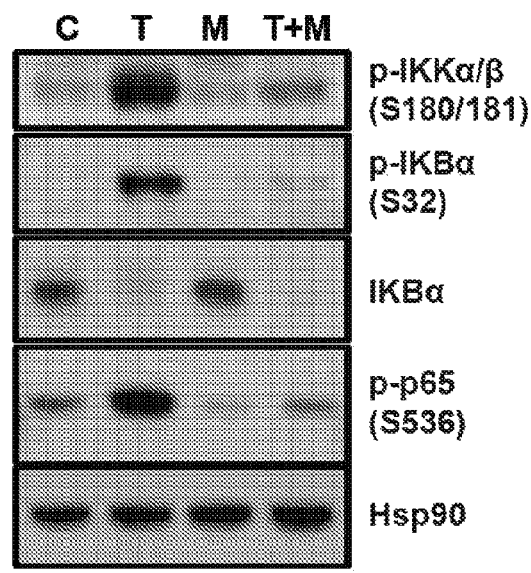
FIG. 16 shows photos of western blot analysis. (A) shows the assessment of NFκB signalling pathway members using (p-IKKα/β (S180/181), p-IKBα (S32), IKBα, p-p65 and (S536), in the following samples: C: Control (DMSO); T: TNFα; M: methotrexate; T+M: TNF-α+methotrexate. Hsp 90 was used as loading control. (B) shows the analysis of immunoprecipitation of NFκB p65 and p50 in the samples C, T, M and T+M. IKBα, p65, p50 levels were observed, and Hsp90 was used as loading control.
Figure 16B:
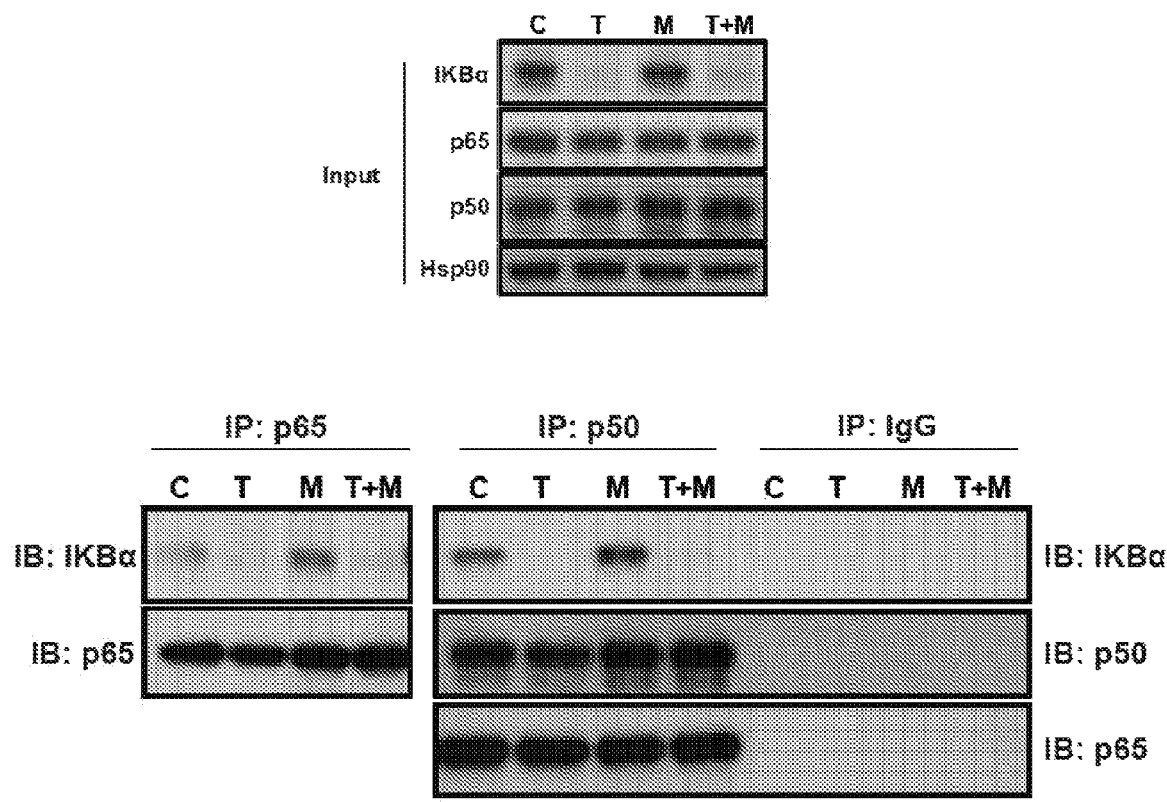

Two of the three identified complexes not known to be implicated in S phase are the MDC1-MRN-ATM-FANCD2 and the DNA ligase III-XRCC-PNK-polymerase III complexes. However, they are involved in the DNA damage response in accordance with the known DNA-damaging effect of methotrexate. The third complex not implicated in S phase is the tumor necrosis factor-α (TNF-α)-nuclear factor kβ (NF-kβ) signalling complex (FIG. 15). It was validated that methotrexate increases the assembly of the associated Ikβα-p65-p50 protein complex by suppressing activation of the NF-kβ signaling pathway, in both the presence and absence of TNF, through inhibiting phosphorylation of the IκB kinase α/β (IKKα/β) complex, IκBα, and p65 in K562 cells (FIGS. 16A and B). Data from both replicates was subsequently combined—the better data coverage and precision allowed more complexes that are differentially modulated between S phase and unsynchronized cells to be uncovered.

Example 4

Figure 17:
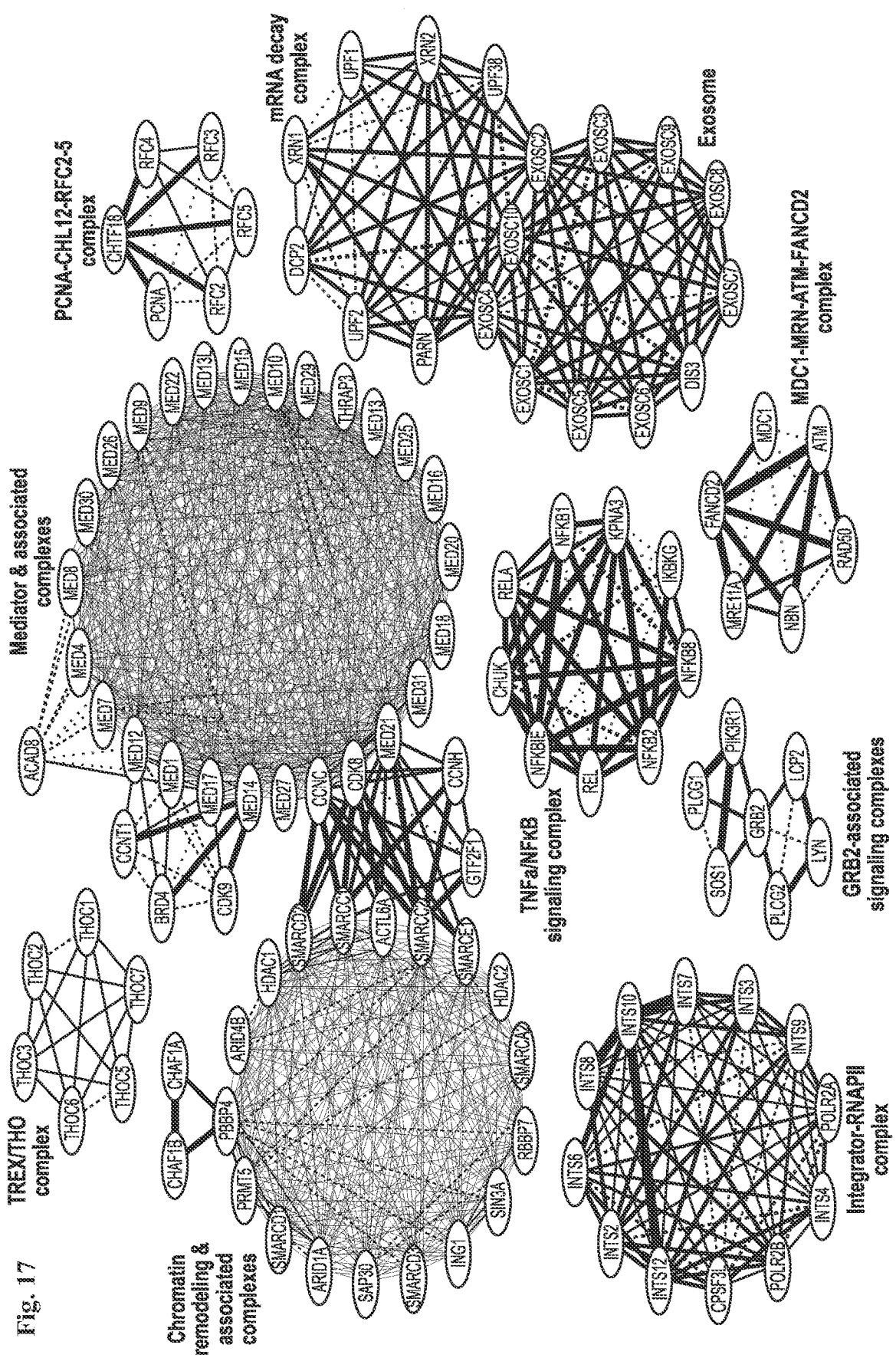
FIG. 17 shows a schematic of a network view of protein complexes with non-random different in PCA behaviour in cells trapped in S phase of cell cycle compared to unsynchronized cells.
Figure 35:
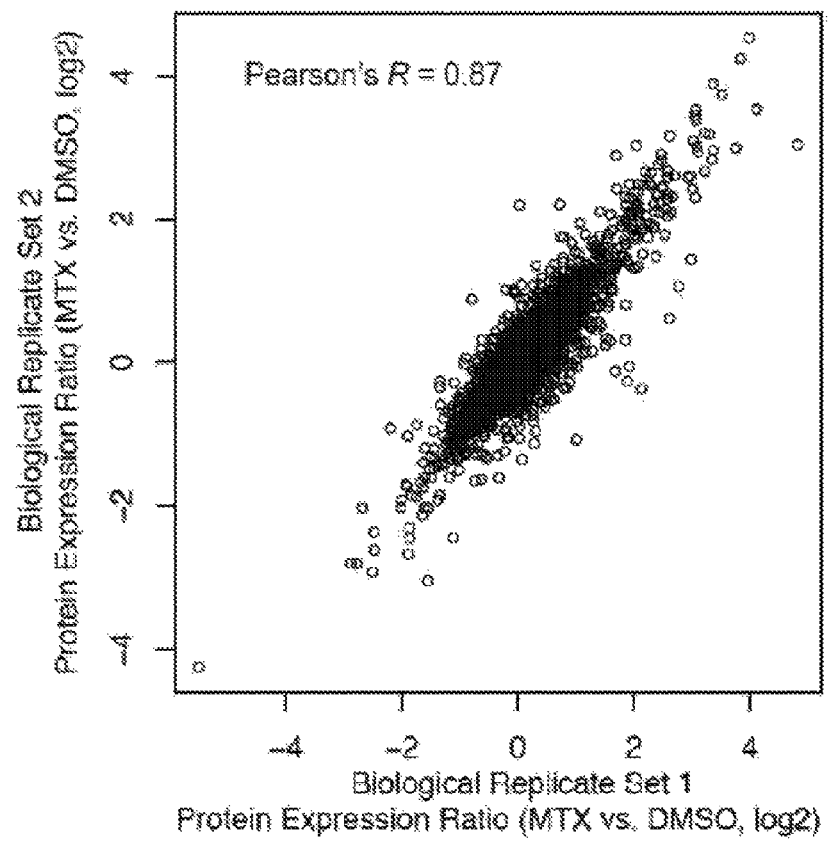
FIG. 35 shows a scatter plot that represents the reproducibility of relative protein expression between DMSO- and methotrexate-treated K562 cells across two biological replicates. The 37° C. samples used to generating melting curves for the experiments were labelled with TMT reagents and analysed by MS.

PCA Signature Across Multiple Cell Lines and Reveals Cell-Specific Interactions and is Predictive of Protein Complexes The enhanced PCA signature of identified complexes largely arose from curve convergence of most subunits (FIG. 17). Nevertheless, this could arise from synchronized changes in protein expression. Thus, relative protein abundance between the DMSO- and methotrexate-treated cells were quantified using MS. High reproducibility in relative abundance (Pearson's R=0.87, FIG. 35) was observed across biological replicates and identified only five subunits (P<0.05, or nine at P<0.1) with differential protein expression (FIG. 17) that are mostly parts of the mediator and integrator megacomplexes. Thus, most subunits exhibit enhanced PCA signature with each other without differential protein expression (FIG. 17).

Figure 18:
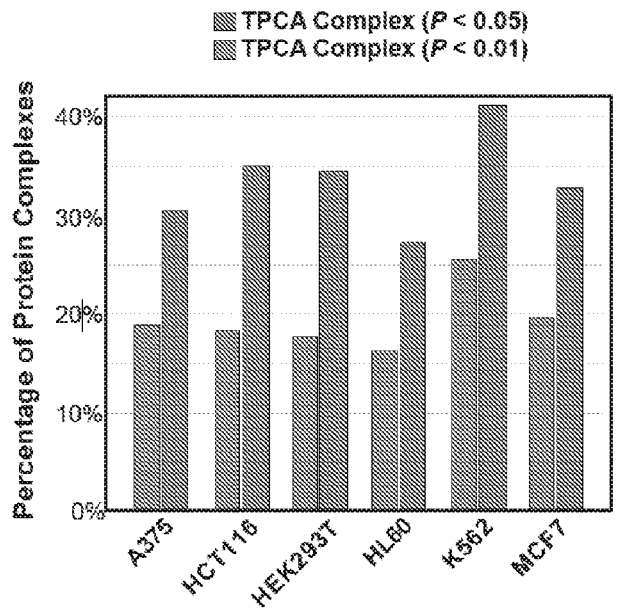
FIG. 18 shows a column graph that represents the number of protein complexes that exhibit PCA complex with P-value<0.05 and P<0.01.
Figure 19:
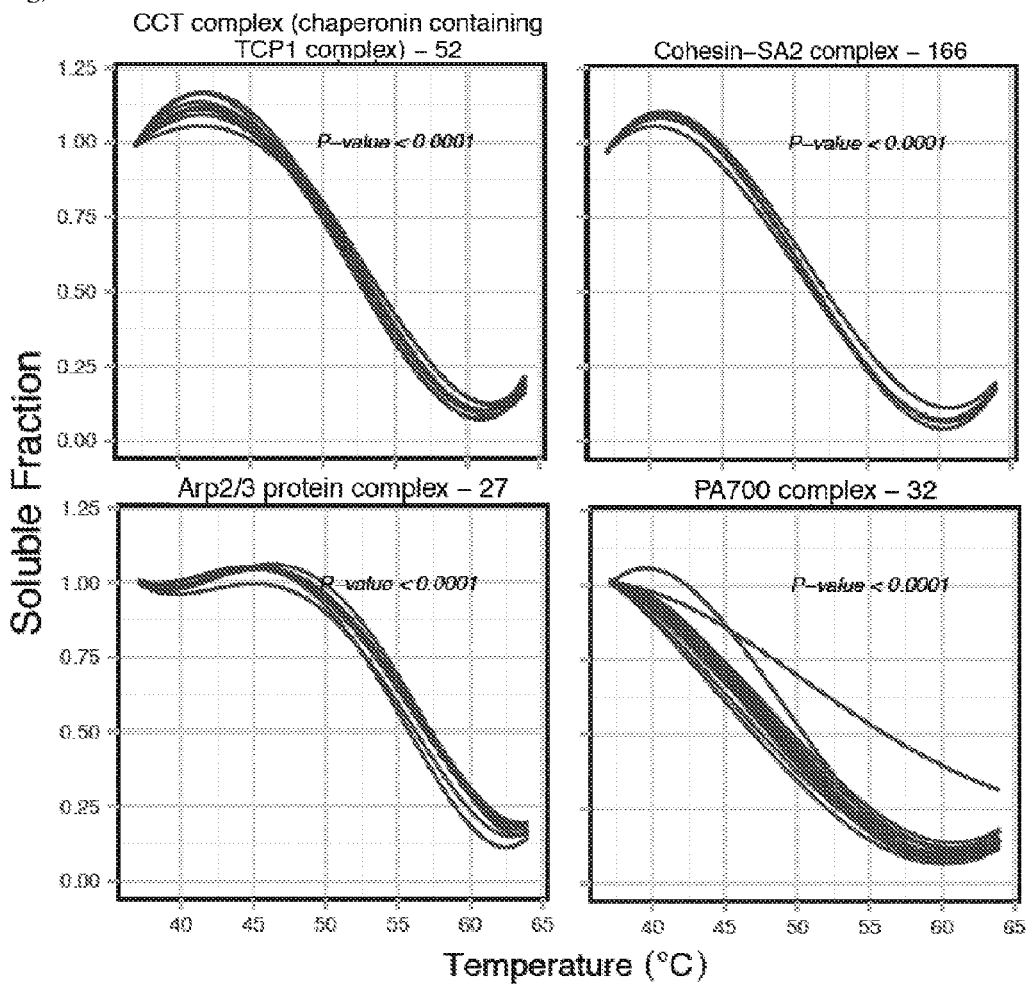
FIG. 19 shows 4 sigmoid graphs that represent the melting curves of selected complexes with strong PCA signature (P-value<0.001). The complexes are CCT complex (chaperonin containing TCP1 complex), Cohesin-SA2 complex, Arp2/3 protein complex and PA700 complex obtained from mouse liver tissue.
Figure 36:
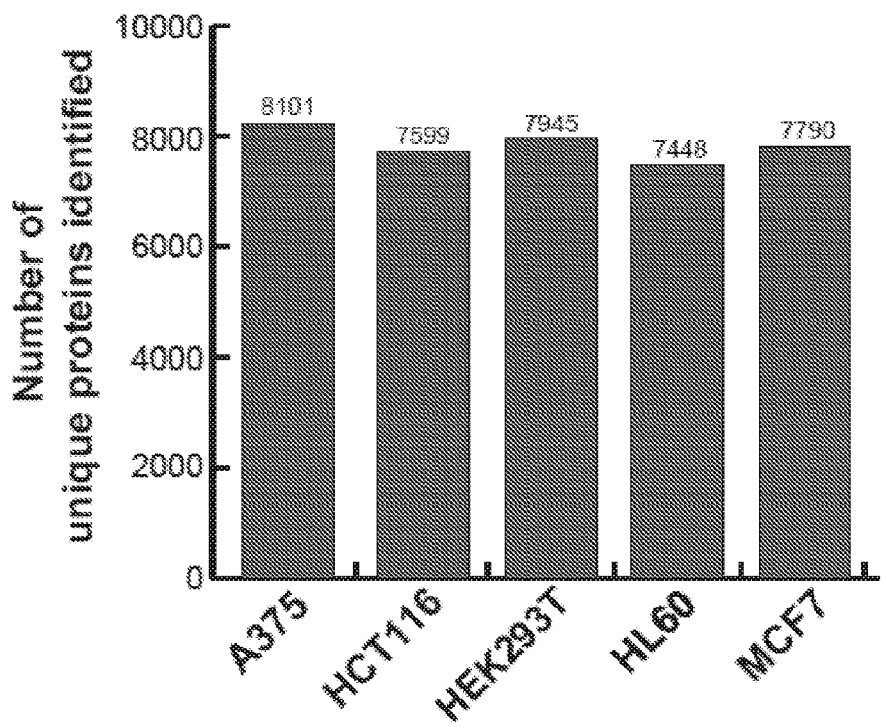
FIG. 36 shows 2 column graphs of MS-CETSA data generated for multiple cell lines. (A) represents the number of protein identified in each cell line profiled. (B) represents the percentage of qualified CORUM complexes (3 or more subunits with melting curves) with non-random PCA signature in each line profiled.
Figure 36:
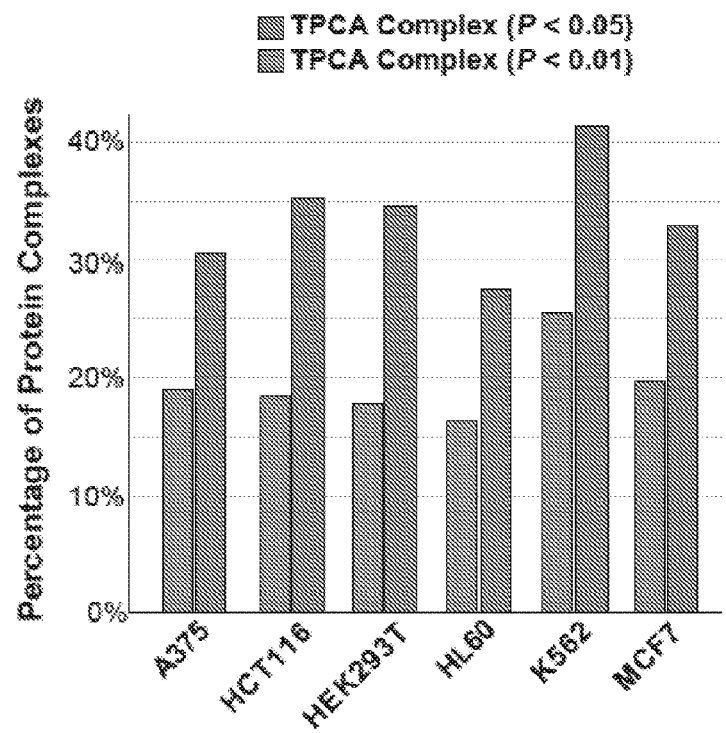
Figure 37:
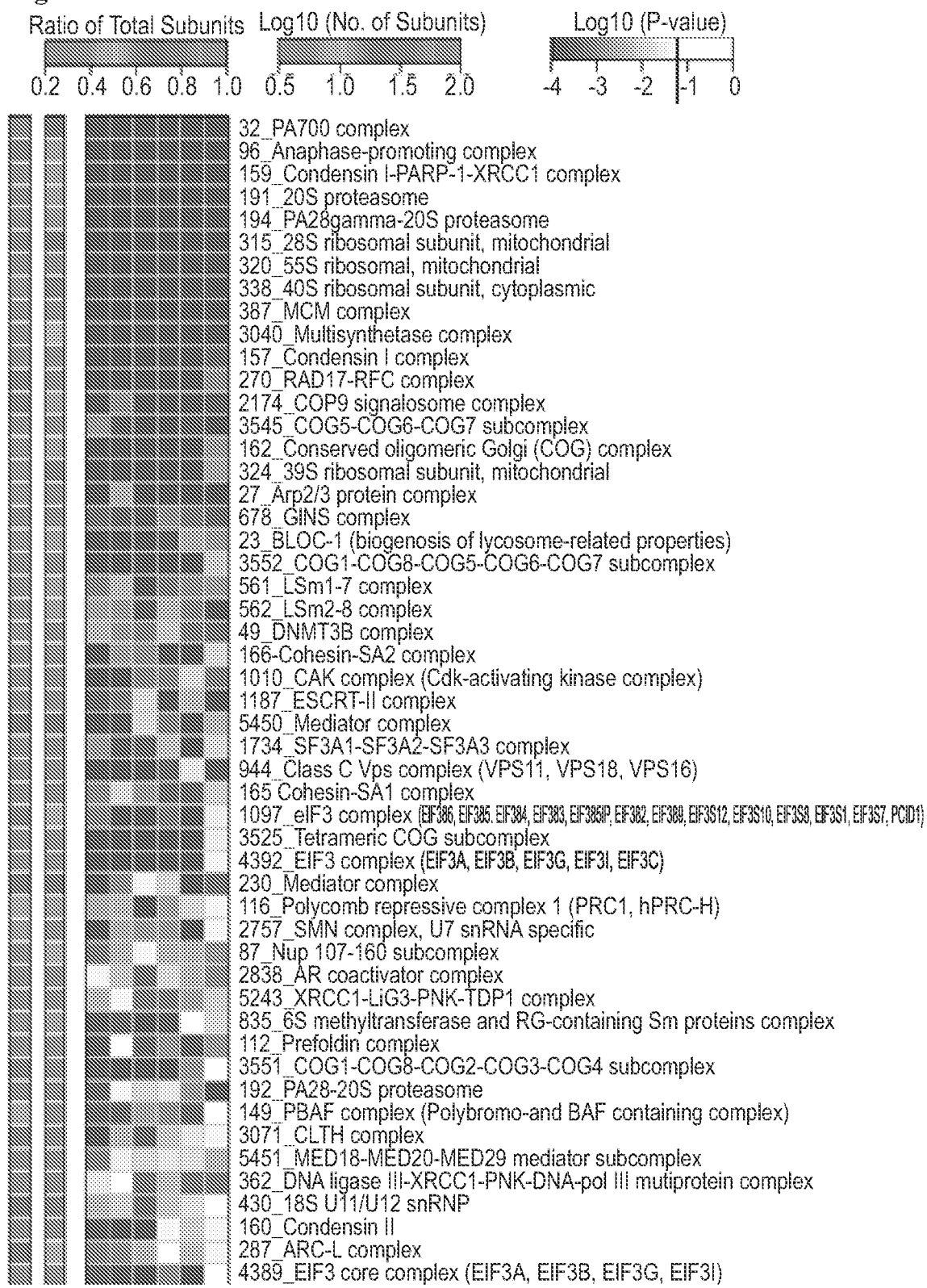
FIG. 37 shows a heatmap of PCA signature for protein complexes with strong PCA signature (P<0.001) in any of the six cell lines. Ratio of subunits refers to the portion of subunits in which melting curves were quantified in our MS-CETSA experiment. The first number to each complex is the CORUM complex identification number.
Figure 37:
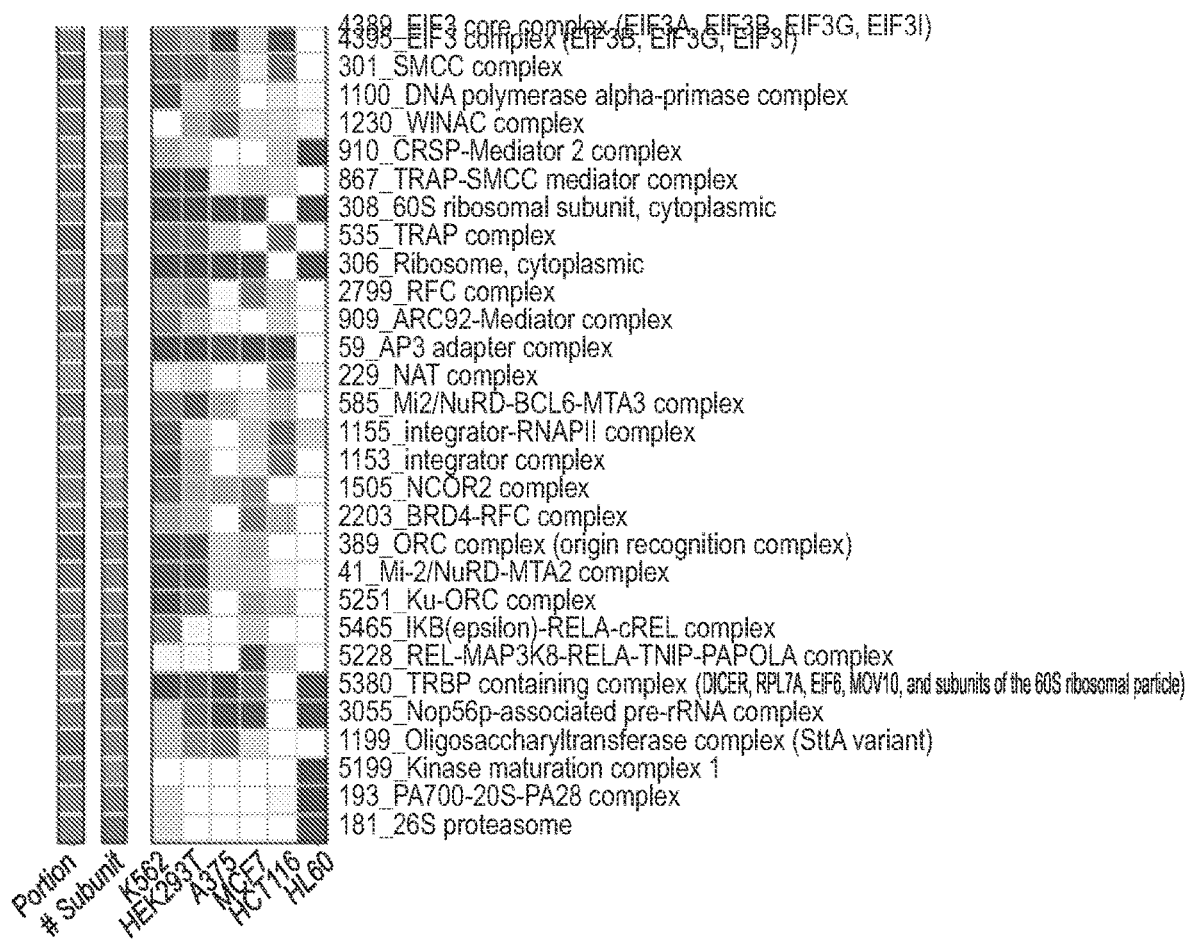
Figure 38:
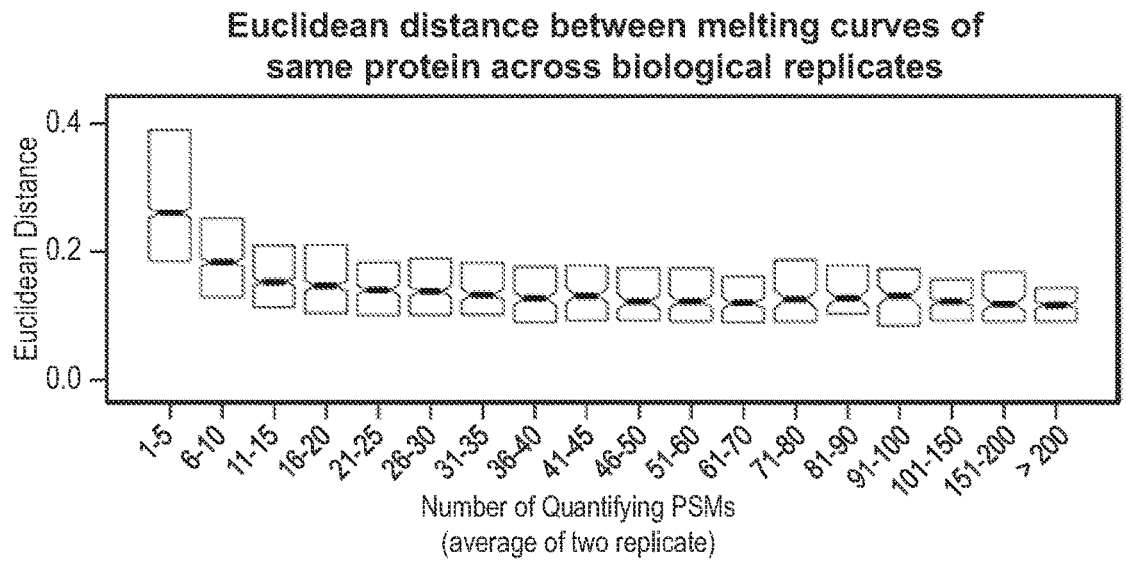
FIG. 38 shows a box plot that represents the Euclidean distance between melting curves of same protein across biological replicates, wherein the curve reproducibility correlates with number of quantifying PSM.
Figure 39:
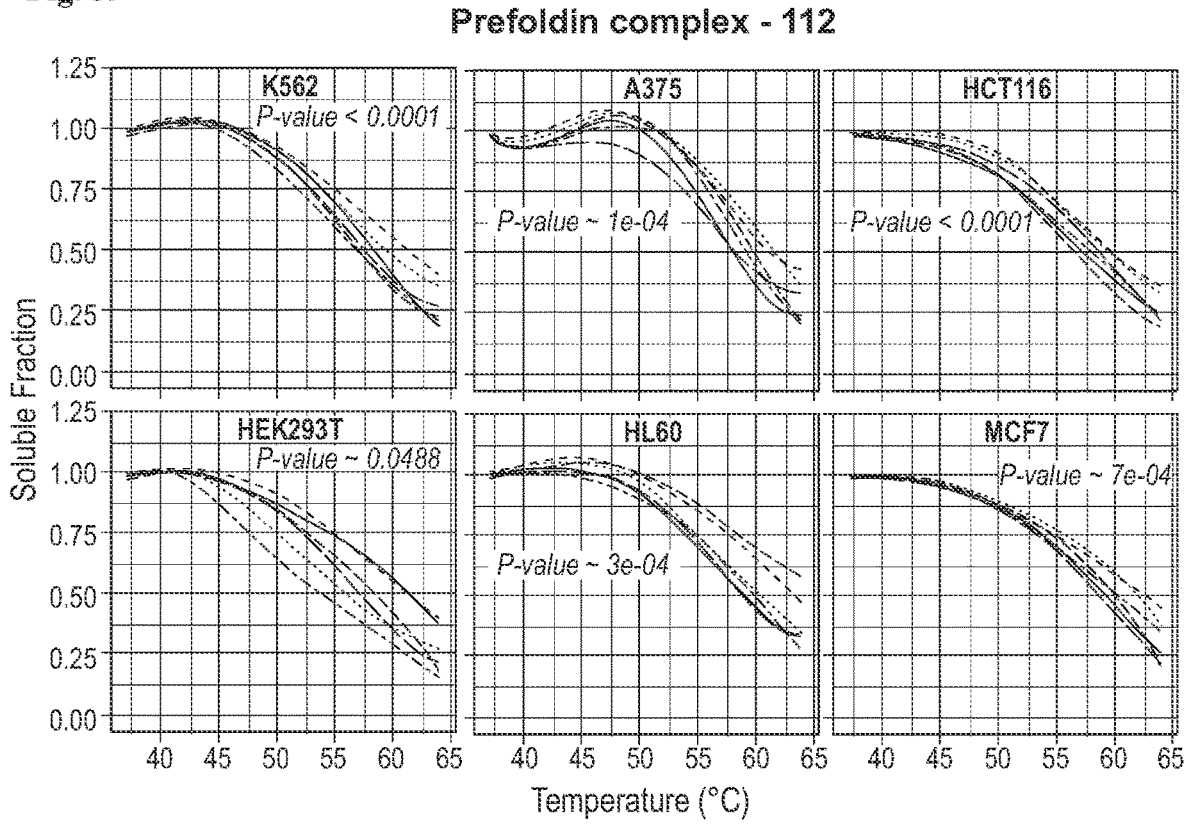
FIG. 39 shows 12 sigmoid curves that represent the melting curves for subunits for the Prefoldin complex and the EIF3 core complex across the six cell lines profiled.
Figure 39:
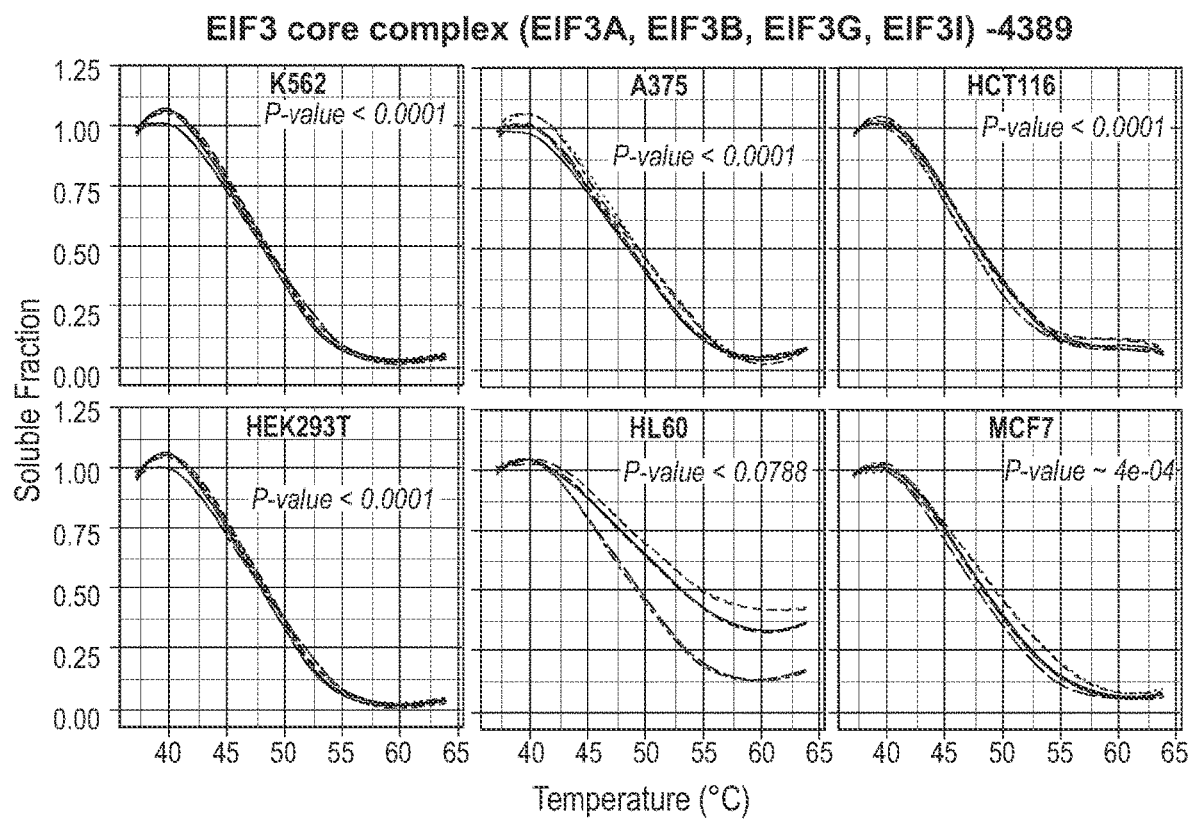

Next, PCA signature was analysed across multiple cell lines. MS-CETSA data was generated from HEK293T, A375, HCT116, MCF7, and HL60 intact cells. Combining data from two biological replicates, each with two technical MS runs (average Pearson's R=0.92 between biological replicates), melting curves were obtained for ~7600 proteins on average for each cell line (FIG. 36A). On average, 33.8% of the qualified CORUM complexes exhibit a non-random PCA signature (P<0.05) in each cell line (FIG. 36B and FIG. 18), with ~70% overlap between cell lines. Data from mouse liver was also obtained and observed ~37.7% of qualified protein complexes (three or more subunits with melting curves) with non-random PCA signatures, including many involved in basal cellular processes (FIG. 19). Thus, PCA is observable across multiple cell lines and from tissue samples. Many protein complexes exhibit strong PCA behaviour across the six cell lines (FIG. 37), but many complexes with high quality but distinct curves across cell lines were also found (FIGS. 38 and 39). This suggests plausible variation in protein complex stoichiometry and composition among cell lines, even for fundamental and abundant protein complexes, that could arise from changes in interaction stoichiometry and/or protein abundance.

Many protein complexes exhibit strong PCA behaviour across the six cell lines including the PA700 proteasome subcomplex and anaphase-promoting complex. Nevertheless, many differentiated complexes were found, including those involved in basal cellular processes such as the EIF3 core complex and the Prefoldin complex. Collating data from a recent large-scale interaction study, it was observed that PCA signature correlates with stoichiometry of protein-protein interaction (FIG. 12B). Thus, the difference in PCA signature observed suggests that protein complex stoichiometry and composition can vary among cell lines even for the most fundamental and abundant complexes. In total, more than 350 CORUM human protein complexes were observed to exhibit significant PCA signature in at least one of the six cell lines.

Figure 20:
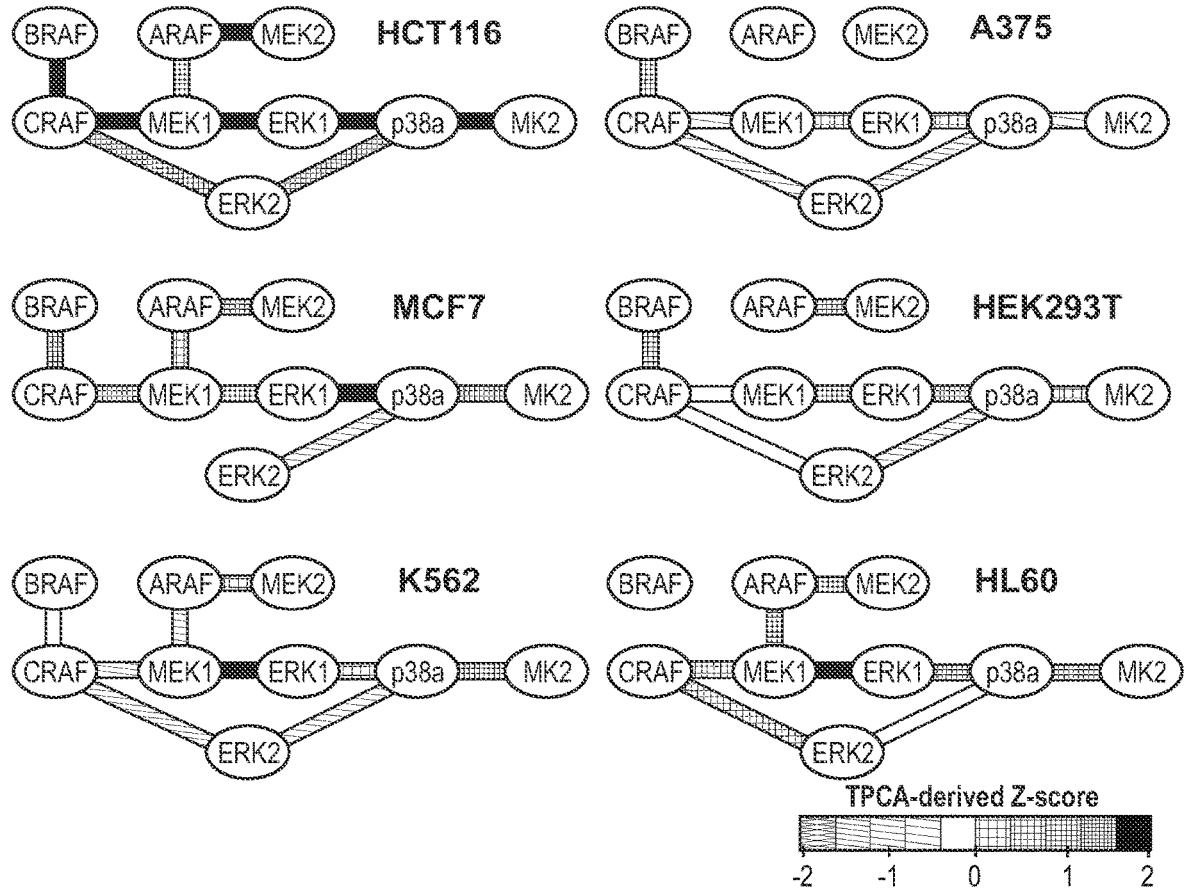
FIG. 20 shows a schematic that represents the PCA analysis reports (based on PCA-derived Z scores) of the differential interactions in the RAF-MEK-ERK pathway in 6 different cell lines, HCT116, A375, MCF7, HEK293T, K562 and HL60. PCA-derived z-scores are used to facilitate comparison of PCA signatures across cell lines. A higher z-score implies increased interactions.
Figure 21:
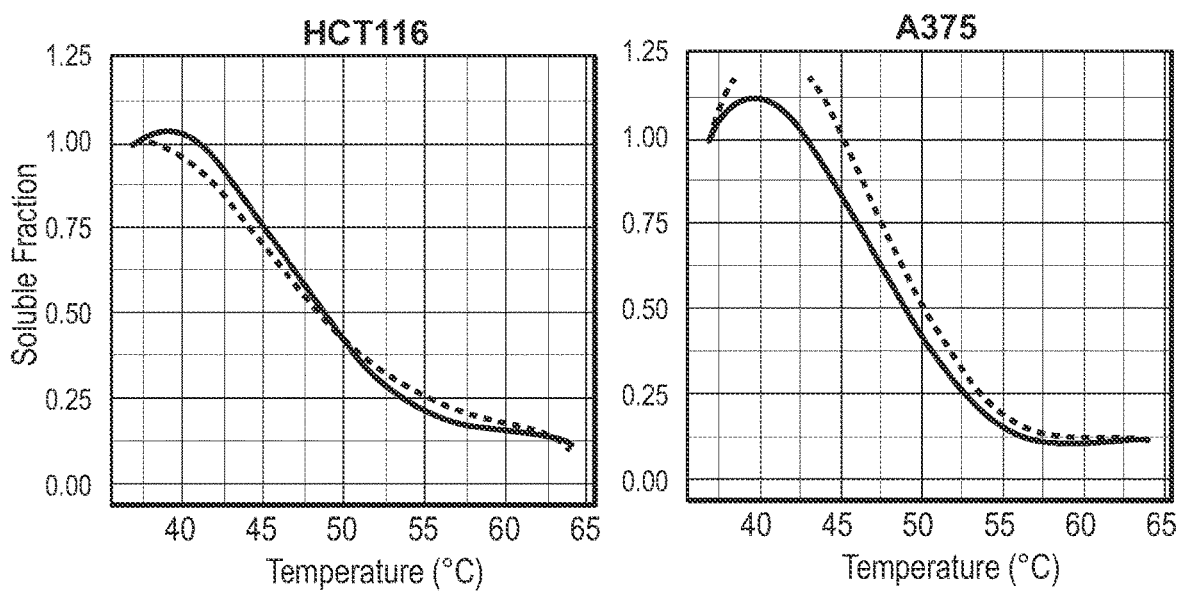
FIG. 21 shows 6 sigmoid graphs that represent the melting curves of RAF1 and BRAF1 in 6 different cell lines, HCT116, A375, MCF7, HEK293T, K562 and HL60.
Figure 21:
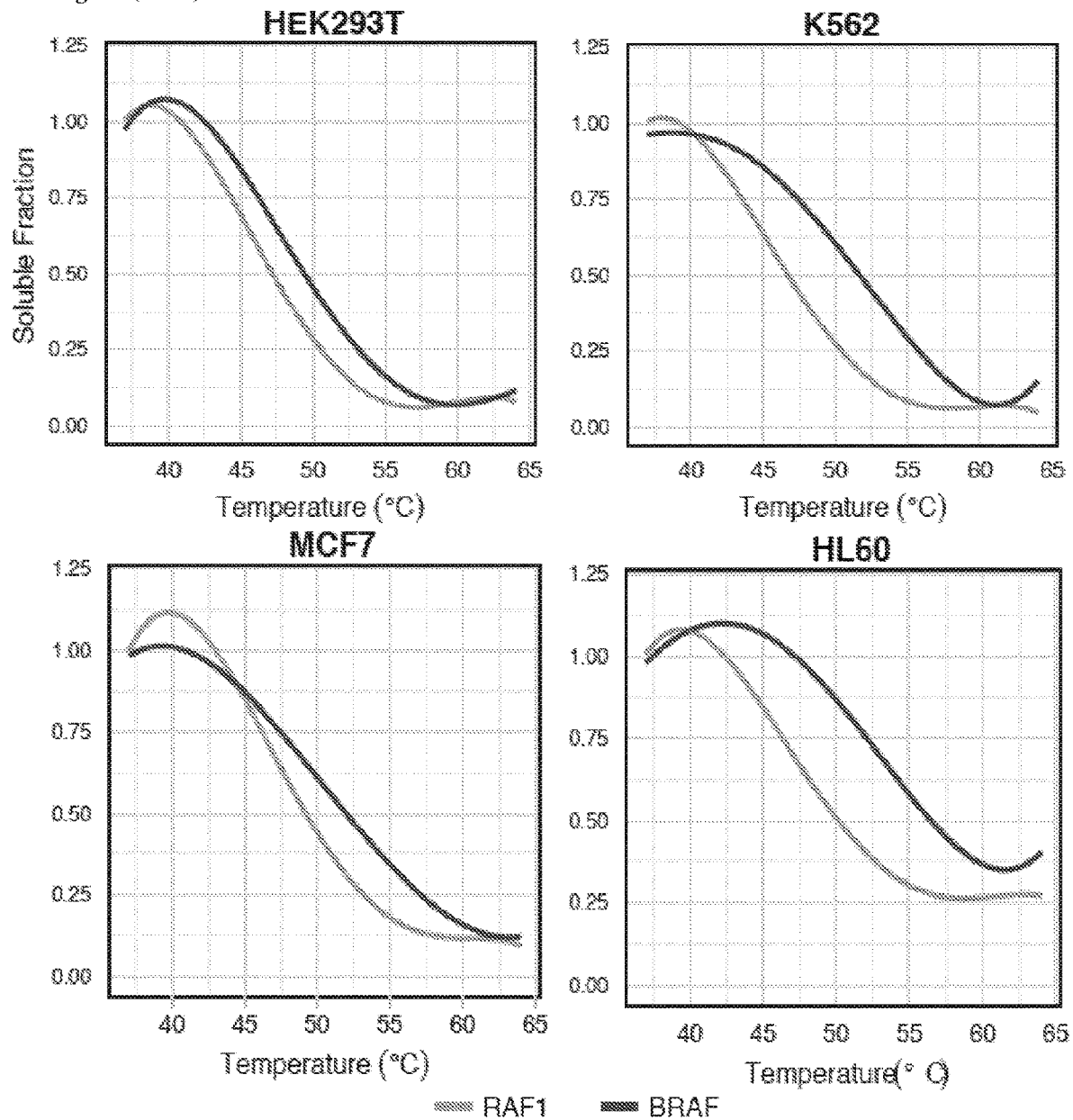

Weighted networks of reported interactions among proteins were identified in all the six cell lines with PCA-derived z-scores were generated. A basal network averaging the z-scores, after removing the highest and the lowest z-scores for each interaction was also constructed. Comparing the basal network with cell-specific PCA-weighted networks facilitates identifying potentially differentiated interactions, pathways, and functional modules. Focusing on HCT116, the RAS-RAF-MEK-ERK pathway was found to contain many interactions with highly differentiated PCA signatures (FIG. 20). Retrospectively, marked similarity in melting curves of BRAF and RAF1 proteins were observed in HCT116 cells compared to other cell lines (FIG. 21), consistent with expected dimerization of BRAF and RAF1 driven by active $KRAS^{G13D}$ in HCT116. PCA analysis also suggests that BRAF-CRAF interaction with MEK is up-regulated in HCT116 cells but is down-regulated in A375 cells, which express $BRAF^{V600E}$ (FIG. 20). This is in line with the recent finding that the interaction is upregulated in cells expressing mutant KRAS and wild-type BRAF but suppressed in cells with mutant BRAF. Thus, PCA could potentially capture cell-specific interactions and pathways.

Figure 22:
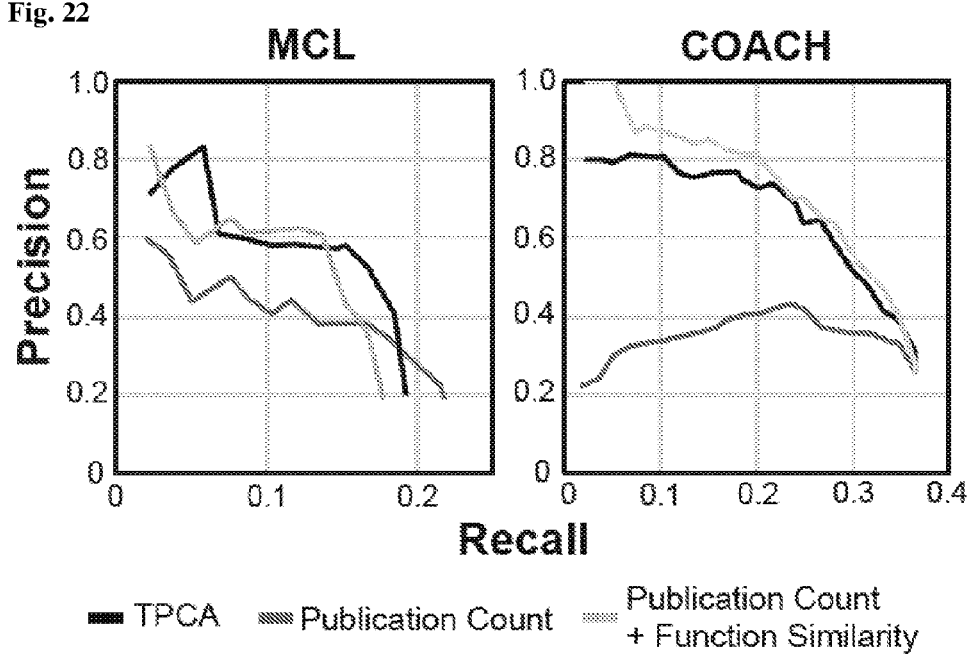
FIG. 22 shows 2 scatter plots that represent data for the prediction of CORUM protein complexes using graph or network clustering algorithms on protein interaction network weighted with publication count, reliability score (publication count+function similarity), and PCA-based scoring. Precision and recall were evaluated against CORUM reference complexes (of size >3) with Jaccard similarity ≥0.5 considered as match.
Figure 23:
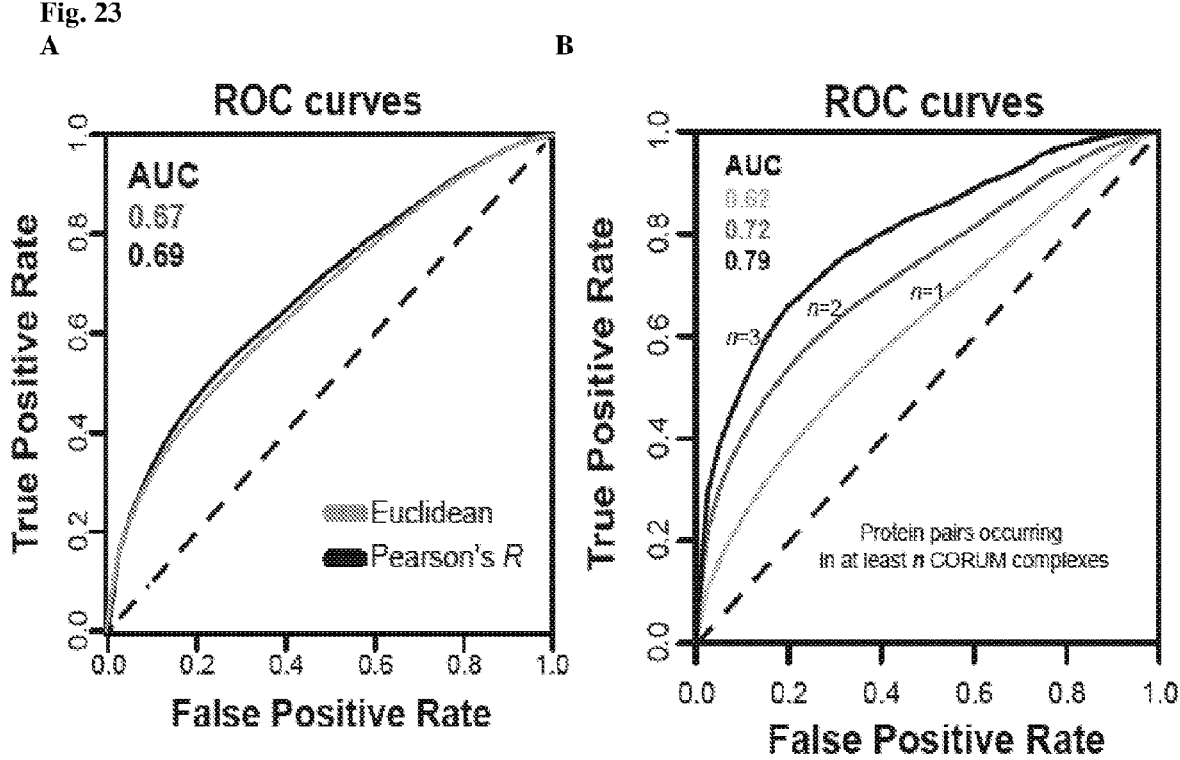
FIG. 23 shows 2 graphical plots that represent receiver operating characteristic curve (ROC). (A) shows data that represent predictability of known interacting protein pairs using PCA. (B) shows data that represent predictability of co-complex pairs using PCA. Melting curve data of intact K562 cells are used. Euclidean distance between all protein pairs with melting curve is computed and ranked by ascending order (lower Euclidean distance first). All protein pairs are considered as negative data except those known to interact or annotated as part of CORUM complexes.

Lastly, it was validated that known and potentially previously unknown protein complexes can be identified from the existing human interactome map using graph or network clustering algorithms with PCA-based scoring of interactions (FIG. 22). The best performance was obtained with the COACH algorithm, which incorporates the core-attachment model of protein complexes. Using this algorithm and PCA based scoring of interactions gives a performance comparable to that of published interaction reliability scores that incorporate publication count and functional similarity. It was also observed that PCA profiling in its current format carries predictive power for protein-protein interactions, with the area under the curve ranging from 0.62 to 0.79 depending on the interaction data sets (FIGS. 23A and B), which collectively suggests that PCA profiles could also serve to discover new interactions and protein complexes in combination with other approaches.

Example 5

Identification of Putative Protein Complexes from Protein Interaction Network with PCA Scoring and Graph/Network Clustering Algorithms The PCA signature is investigated whether it can be used to predict known and validated protein complexes from assembled protein-protein interaction networks. Specifically, each interacting protein pairs in an assembled protein-protein interaction network is weighted with PCA-derived scores (as $1/(1+E)$ where E is Euclidean distance between two melting curves), and assess their capacity to assist three network/graph clustering algorithms (namely CMC, ClusterOne, and MCL to identify protein complexes annotated in CORUM. This is much like many previous projects which scored their derived protein-protein interaction data and used existing graph/network clustering algorithms to identify known and putative protein complexes. However, unlike previous projects that use machine learning classifiers to integrate multiple orthogonal data and calibrated for optimal result with gold standards like CORUM and STRING, each interacting protein pairs was scored solely using PCA without training datasets or gold standards for calibration. Two other network/graph clustering algorithms, COACH and IPCA, that accept unweighted network as input were also tested, but the predicted complexes were subsequently ranked according to their weighted density (sum of edge weights in the predicted complex/number of possible edges in the predicted complex).

To improve the coverage of protein complexes, especially for those that are cell- or condition-specific, PCA data from all the six cell lines profiled at basal state were used, obtaining the final PCA-derived score for each interaction from the average of two best scores from the six cell lines profiled. For baseline comparison, the reliability/confidence of each interacting protein pairs are scored based on their number of reporting publications normalized to the highest publication count. However, interacting protein pairs reported by at least 2 publications were used as it is found that the resulting protein network favours the identification, and ranked highly CORUM complexes across the five network/graph clustering algorithms used. For each algorithm, the same sets of parameters are tested and selected the best AUC (Area Under Curve) for each weighted network.

It is observed that the PCA-weighted protein-protein interaction network gives significantly better performance in three out of the five algorithms tested compared to publication-based scoring while the performance is comparable for the remaining algorithms. The best improvement in performance with PCA is obtained with the COACH algorithm. Interestingly, the COACH algorithm explicitly exploits the core-attachment model to enhance the identification of protein complexes from protein interaction network, by first identifying the complex cores following by identifying attachment subunits subsequently. With PCA-based scoring of the complexes predicted by COACH, the top hits for the known and validated CORUM complexes are enriched. The complexes that are identified with high coverage (75% or more subunits identified) by COACH and ranked highly by PCA include multisynthetase complex, PA700-20S-PA28 complex, MCM complex, conserved oligomeric golgi (COG) complex, condensin complex and the TREX/THO complexes.

Next, the PCA-based scoring is compared with a previously published interaction reliability scoring scheme that combine publication count and the coherency of each reporting experimental methods to identify interacting protein pairs from the same cellular component and/or protein complex. The coherency of different experimental method is computed as the fraction of detected interacting protein pairs where both proteins share a high-level cellular-component Gene Ontology (GO) term. For each interacting protein pair, the final reliability score is formulated using a Noisy-Or model:

$$\text{Reliability}_{(a,b)} = 1 - \Pi_{e \in X(a,b)}(1-coh)^{n_{e,(a,b)}}$$

where $X(a, b)$ is the set of experimental methods that detected interaction $(a, b)$ between protein a and b, and $n_{e,(a,b)}$ is the number of times experimental method e detected interaction $(a, b)$.

PCA performances across the five algorithms are observed to be very similar to using interaction reliability scoring scheme that incorporate publication frequency and indirectly co-localization or co-complex information. Thus, PCA scoring with existing protein-protein interaction data can predict known and validated protein complexes across different network/graph clustering algorithms, that is comparable with using publication count and existing annotation. In addition, combining PCA with other orthogonal evidence can plausibly further improve prediction of annotated protein complexes.

In summary, PCA enables the intracellular study of the dynamics of multiple protein complexes simultaneously in intact nonengineered cells and tissues. About one-third of the qualified CORUM complexes in each cell line exhibit non-random PCA signatures, with 58% of the complexes exhibiting non-random PCA signatures in at least one of the cell lines profiled. Membrane-embedded complexes are included in CORUM but are likely not amenable to the other protocols. Nonsignificant PCA signatures could arise for protein complexes with very low interaction stoichiometry—increased assembly can be monitored by changes in PCA signature. PCA profiling suggests that many complexes can remain intact yet thermally destabilized in the absence of interaction with DNA and LMW ligands such as ATP (FIGS. 6 and 10). Many mitochondrial proteins are observed to be more temperature resistant in intact cells.

This study shows that PCA constitutes an approach for system-wide studies of protein interaction.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method for identifying a protein interaction between one or more first proteins and one or more further proteins, said method comprising the steps of:
    a) exposing one or more samples comprising the one or more first proteins and said one or more further proteins to at least one preselected condition for at least one preselected duration;
    b) isolating and separating at least one soluble fraction from an insoluble fraction of said one or more samples;
    c) determining and comparing the solubility of the one or more first proteins to the solubility of the one or more further proteins in the at least one soluble fraction or the insoluble fraction of step b); and,
    d) determining similarity in solubility between the one or more first proteins and one or more further proteins in said one or more samples, wherein a non-random increase in similarity in solubility is indicative of a protein interaction between said one or more first proteins and said one or more further proteins in said one or more samples.

2. The method as claimed in claim 1, wherein the at least one preselected condition in step a) is a preselected temperature; optionally wherein the at least one preselected temperature is capable of causing a change in precipitation of the first protein when interacting with one or more further proteins compared to the first protein when not interacting with one or more further proteins.

3. The method as claimed in claim 1, wherein the first protein in said one or more samples is comprised within or on cells.

4. The method as claimed in claim 1, wherein the one or more samples is a biological sample.

5. The method as claimed in claim 4, wherein said biological sample is an intact cell or a cell lysate.

6. The method as claimed in claim 5, wherein the one or more samples is an intact cell.

7. The method as claimed in claim 1, wherein the one or more samples is or are obtained from the same sample or different samples.

8. The method as claimed in claim 5, wherein the one or more samples is or are modified prior to use in said method.

9. The method as claimed in claim 1, wherein the first protein or the one or more further proteins is or are wild-type or recombinant proteins.

10. The method as claimed in claim 1, wherein step b) comprises the step of lysing the cell to obtain a cell lysate prior to isolating and separating the at least one soluble fraction from the insoluble fraction.

11. The method as claimed in claim 10, wherein step b) further comprises the step of centrifuging or filtering the cell lysate to obtain a supernatant fraction prior to isolating and separating the at least one soluble fraction from an insoluble fraction.

12. The method as claimed in claim 1, wherein step d) further comprises obtaining a proximity co-aggregation (PCA) signature to identify said protein interaction between one or more first proteins and one or more further proteins in said one or more samples.

13. The method as claimed in claim 1, wherein the similarity in solubility between one or more first proteins and said one or more further proteins in said one or more samples is determined by comparison to a reference.

14. The method as claimed in claim 13, wherein the reference is the solubility similarity of a random group of proteins in the same sample.

15. The method as claimed in claim 13, wherein the reference is the solubility similarity of said one or more first proteins and said one or more further proteins in a different sample.

16. The method as claimed in claim 1, wherein the solubility is obtained by mass spectrometry.

17. The method as claimed in claim 1, wherein step d) comprises determining the average distance between the solubility of the one or more first proteins to the solubility of the one or more further proteins using one or more distance metrics and using said distance as an inverse measure of solubility similarity between the putative interacting proteins and non-interacting protein.

18. The method as claimed in claim 17, wherein the distance metric is Euclidean distance or Pearson's correlation coefficient.

19. Use of the method according to claim 1 for screening for therapeutic drug targets, disease progression prognosis, determining efficacy of drug therapies, determining protein stoichiometry, identifying novel protein pathways, mapping protein interactomes, predicting protein function, or mapping temporal protein interactions.

* * * * *